(12) United States Patent
Ritz et al.

(10) Patent No.: US 12,268,426 B2
(45) Date of Patent: Apr. 8, 2025

(54) ORTHOPEDIC TORSION GENERATED COMPRESSION IMPLANTS AND METHODS FOR USING SAME

(71) Applicants: Joseph Paul Ritz, Castroville, TX (US); Eric Alberto Marcano, San Antonio, TX (US)

(72) Inventors: Joseph Paul Ritz, Castroville, TX (US); Eric Alberto Marcano, San Antonio, TX (US)

(73) Assignee: 210 DYNAMIC, LLC, San Antonio, TX (US)

( * ) Notice: Subject to any disclaimer, the term of this patent is extended or adjusted under 35 U.S.C. 154(b) by 252 days.

(21) Appl. No.: 17/465,648

(22) Filed: Sep. 2, 2021

(65) Prior Publication Data

US 2022/0061837 A1    Mar. 3, 2022

Related U.S. Application Data

(60) Provisional application No. 63/074,346, filed on Sep. 3, 2020.

(51) Int. Cl.
  *A61B 17/88*    (2006.01)
  *A61B 17/064*   (2006.01)
  (Continued)

(52) U.S. Cl.
  CPC .......... *A61B 17/88* (2013.01); *A61B 17/0642* (2013.01); *A61B 17/0644* (2013.01);
  (Continued)

(58) Field of Classification Search
  CPC ............ A61B 17/0642; A61B 17/0644; A61B 2017/0645; A61B 17/8004; A61B 17/809; A61B 17/88
  See application file for complete search history.

(56) References Cited

U.S. PATENT DOCUMENTS 4,887,601 A      12/1989  Richards
5,474,557 A  *   12/1995  Mai ....................... A61B 17/68
                                                        606/78

(Continued)

FOREIGN PATENT DOCUMENTS

CN    105213072 A    1/2016
EP    3479779 A1     5/2019

(Continued)

OTHER PUBLICATIONS

PCT/US2021/048919 International Search Report and Written Opinion dated Dec. 23, 2021 (14 p.).

(Continued)

*Primary Examiner* — Larry E Waggle, Jr.
(74) *Attorney, Agent, or Firm* — CONLEY ROSE, P.C.

(57) ABSTRACT

An example orthopedic implant includes a bridge, a plurality of torsion regions coupled to the bridge, and a plurality of legs coupled to and extending from the plurality of torsion regions. The plurality of legs are configured to transition between a first position and a second position, and in the second position, the plurality of legs are angularly displaced relative to the first position. In addition, the legs are biased toward the first position by elastic torsional stresses in the plurality of torsion regions when the legs are in the second position.

4 Claims, 14 Drawing Sheets

(51) Int. Cl.
*A61B 17/00* (2006.01)
*A61B 17/56* (2006.01)

(52) U.S. Cl.
CPC ............... *A61B 2017/00867* (2013.01); *A61B 2017/0641* (2013.01); *A61B 2017/564* (2013.01)

(56) References Cited

U.S. PATENT DOCUMENTS

| | | | |
|---|---|---|---|
| 6,554,852 | B1 | 4/2003 | Oberlander |
| 7,618,441 | B2 * | 11/2009 | Groiso ............... A61B 17/7059 606/301 |
| 7,850,797 | B2 * | 12/2010 | Carley ................. A61B 17/083 148/563 |
| 8,062,297 | B2 * | 11/2011 | Faillace ............. A61B 17/0642 606/75 |
| D705,930 | S | 5/2014 | Cheney |
| 8,951,254 | B2 | 2/2015 | Mayer et al. |
| 9,402,624 | B1 * | 8/2016 | Scott .................... A61B 17/064 |
| 9,408,594 | B2 * | 8/2016 | LaBombard ....... A61B 17/0057 |
| 10,016,198 | B2 * | 7/2018 | Morgan ................. A61B 17/10 |
| 10,117,647 | B2 * | 11/2018 | Cheney ............. A61B 17/0642 |
| 10,335,219 | B2 | 7/2019 | Mayer |
| 10,820,902 | B2 | 11/2020 | Cheney |
| 11,006,949 | B2 | 5/2021 | Daniel |
| 11,020,110 | B1 | 6/2021 | Blair et al. |
| 11,116,499 | B1 | 9/2021 | Blair et al. |
| 11,571,206 | B2 | 2/2023 | Coleman et al. |
| 2007/0225762 | A1 | 9/2007 | Labombard |
| 2008/0015598 | A1 | 1/2008 | Prommersberger |
| 2011/0022099 | A1 * | 1/2011 | Ashman ............... A61B 17/823 606/331 |
| 2011/0313437 | A1 | 12/2011 | Yeh |
| 2012/0241504 | A1 | 9/2012 | Soltz et al. |
| 2013/0168432 | A1 | 7/2013 | Vold et al. |
| 2013/0184768 | A1 | 7/2013 | McIff et al. |
| 2014/0276830 | A1 | 9/2014 | Cheney |
| 2017/0196678 | A1 | 7/2017 | Park et al. |
| 2019/0192140 | A1 | 6/2019 | Ducharme et al. |
| 2020/0000465 | A1 | 1/2020 | Maclure et al. |

FOREIGN PATENT DOCUMENTS

| | | |
|---|---|---|
| WO | 2015-099997 A1 | 7/2015 |
| WO | 2017-155921 A2 | 9/2017 |
| WO | 2019/207585 A1 | 10/2019 |
| WO | 2021/202008 A1 | 10/2021 |

OTHER PUBLICATIONS

European Search Report dated Jul. 26, 2024, for European Application No. 21865134.7 (8 p.).

* cited by examiner

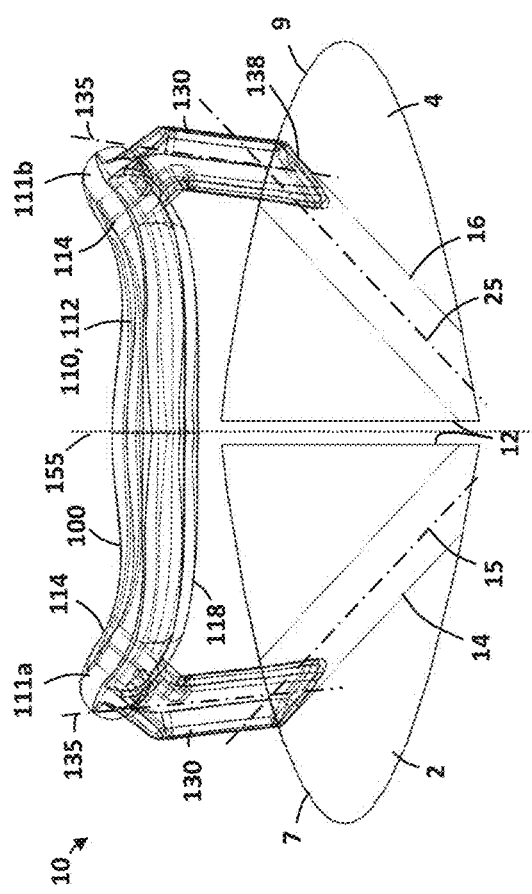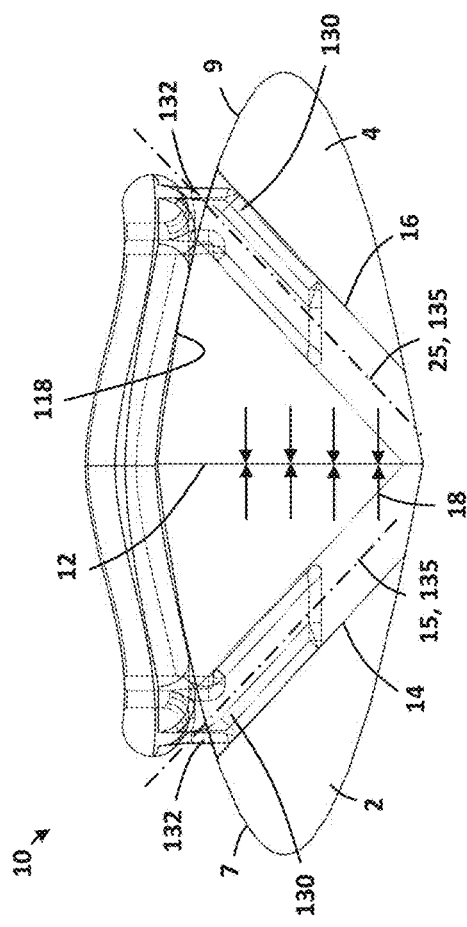

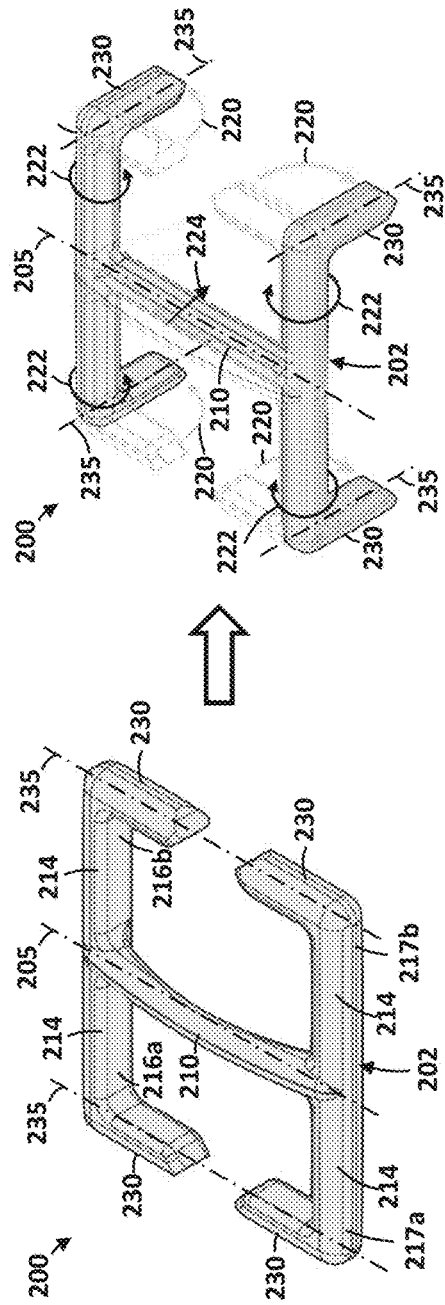
FIG. 6A
FIG. 6B
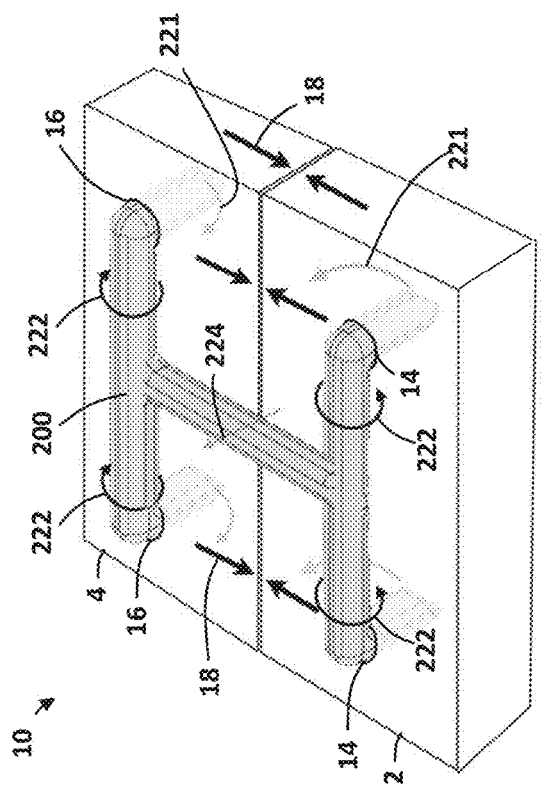
FIG. 7

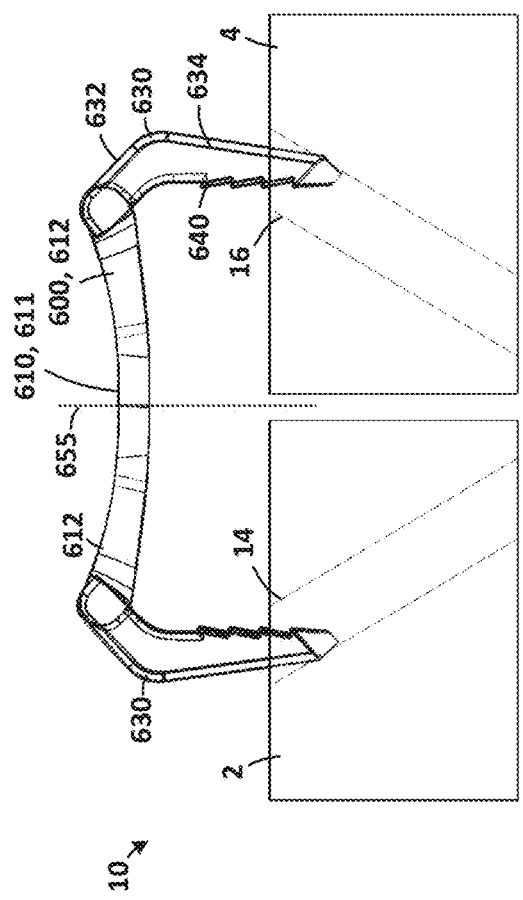
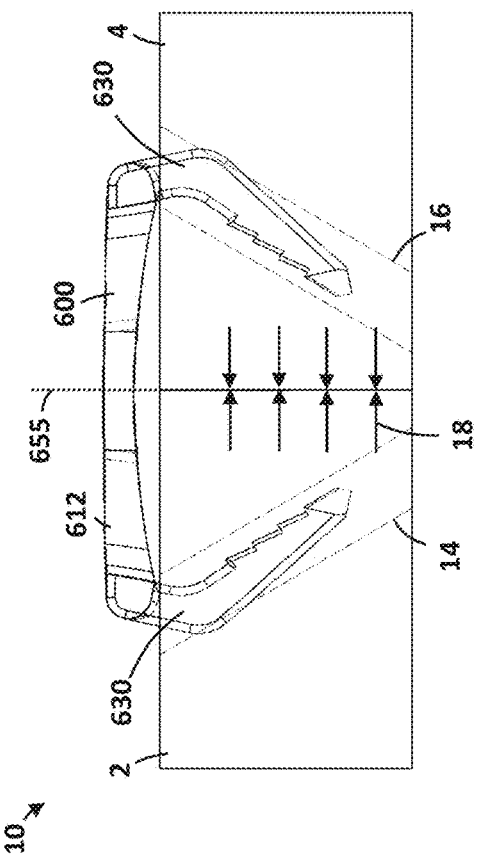

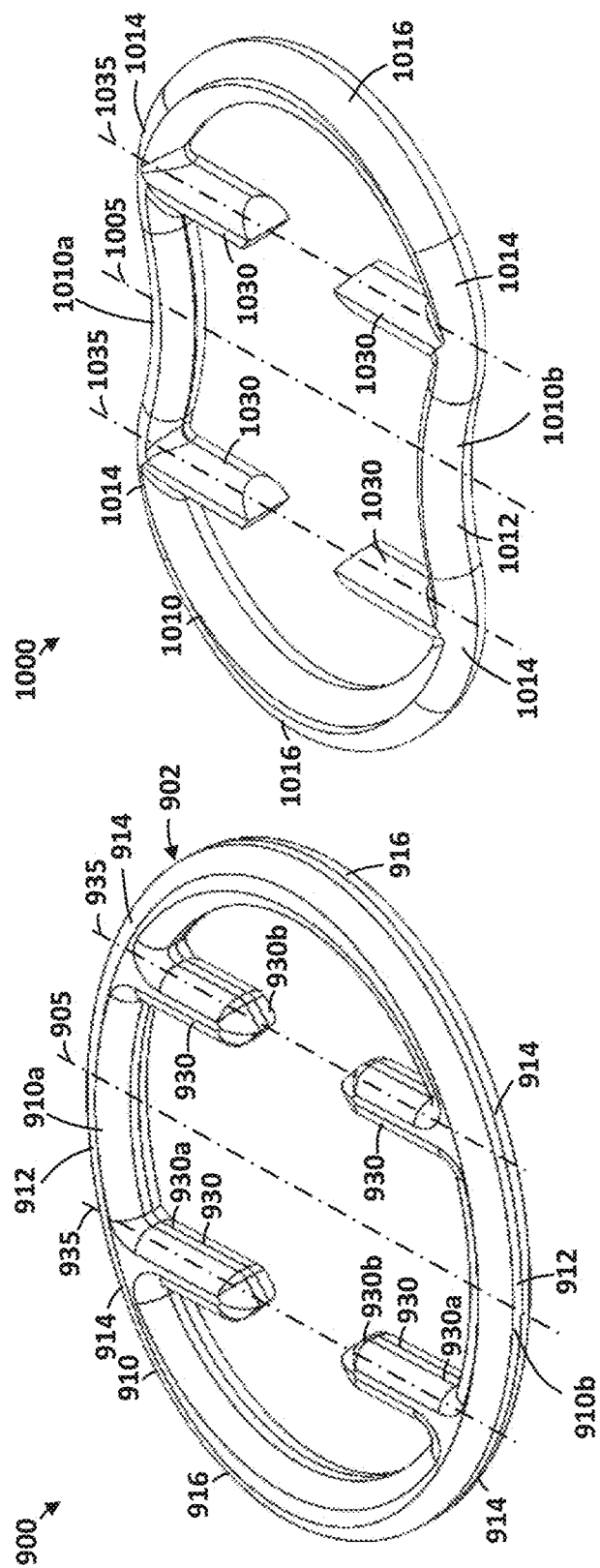

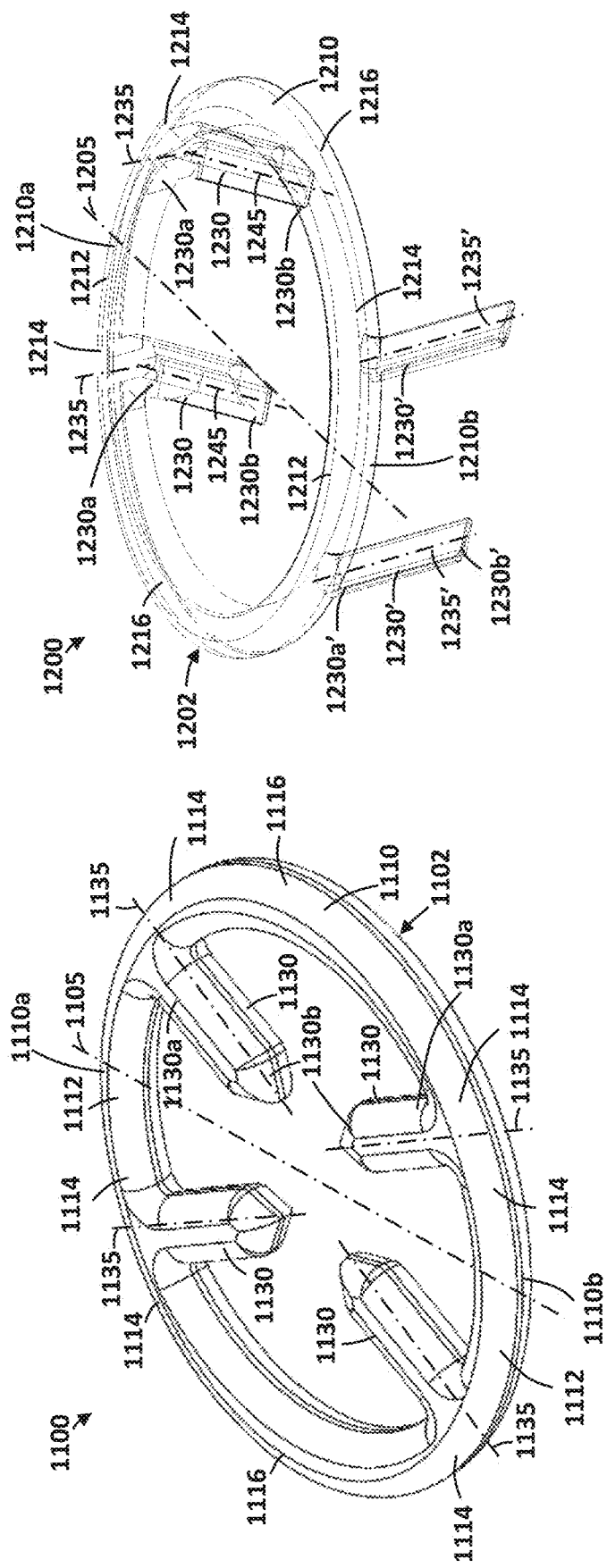

ORTHOPEDIC TORSION GENERATED COMPRESSION IMPLANTS AND METHODS FOR USING SAME

CROSS-REFERENCE TO RELATED APPLICATIONS

This application claims benefit of U.S. provisional patent application Ser. No. 63/074,346 filed Sep. 3, 2020, and entitled "Orthopedic Torsion Generated Compression Implants," which is hereby incorporated herein by reference in its entirety.

STATEMENT REGARDING FEDERALLY SPONSORED RESEARCH OR DEVELOPMENT

Not applicable.

BACKGROUND

Staple-style orthopedic implants are often used to provide fixation and stability at a fracture, osteotomy or arthrodesis site to facilitate and enable fusion. Some orthopedic implants are shape memory compression implants that may change dimensions or geometry as a function of temperature to offer greater fixation and stability to enable fusion.

BRIEF SUMMARY

Some embodiments disclosed herein are directed to an orthopedic implant. In an embodiment, the orthopedic implant includes a bridge, a plurality of torsion regions coupled to the bridge, and a plurality of legs coupled to and extending from the plurality of torsion regions. The plurality of legs are configured to transition between a first position and a second position, and in the second position, the plurality of legs are angularly displaced relative to the first position. In addition, the legs are biased toward the first position by elastic torsional stresses in the plurality of torsion regions when the legs are in the second position.

Some embodiments disclosed herein are directed to an orthopedic staple. In an embodiment, the orthopedic staple includes a body comprising a plurality of torsion regions and a second region. In addition, the orthopedic staple includes a plurality of legs coupled to the plurality of torsion regions. An angular displacement of the legs is configured to induce a torsional stress in the torsional regions and a bending stress in the second region.

Some embodiments disclosed herein are directed to a method for installing an orthopedic implant comprising a body and a plurality of legs coupled to the body. In an embodiment, the method includes (a) applying a torsional stress to the body that imparts a first angular displacement between the plurality of legs. In addition, the method includes (b) inserting the plurality of legs into a plurality of holes in a pair of bone segments. Further, the method includes (c) releasing the body after (b) such that the torsional stresses impart a second angular displacement between the plurality of legs, wherein the second angular displacement is opposite the first angular displacement.

Embodiments described herein comprise a combination of features and characteristics intended to address various shortcomings associated with certain prior devices, systems, and methods. The foregoing has outlined rather broadly the features and technical characteristics of the disclosed embodiments in order that the detailed description that follows may be better understood. The various characteristics and features described above, as well as others, will be readily apparent to those skilled in the art upon reading the following detailed description, and by referring to the accompanying drawings. It should be appreciated that the conception and the specific embodiments disclosed may be readily utilized as a basis for modifying or designing other structures for carrying out the same purposes as the disclosed embodiments. It should also be realized that such equivalent constructions do not depart from the spirit and scope of the principles disclosed herein.

BRIEF DESCRIPTION OF THE DRAWINGS

For a detailed description of various exemplary embodiments, reference will now be made to the accompanying drawings in which:

FIG. 3 is a side view of the implant of FIG. 2 in a flexed position as the implant is positioned across two bone segments;

FIG. 4 is a side view of the implant of FIG. 2 in a partially flexed position as the implant compresses the two bone segments together;

FIGS. 6A and 6B are isometric views of the implant of FIG. 5 illustrating bending deflections and torsional displacements between an un-flexed position (FIG. 6A) and a flexed position (FIG. 6B);

FIG. 7 is an isometric view of the implant of FIG. 5 in a partially flexed position compressing two bone segments together;

FIG. 13 is a side view of the implant of FIG. 12 in a flexed position as the implant is positioned across two bone segments;

FIG. 14 is a side view of the implant of FIG. 12 in a partially flexed position as the implant compresses the two bone segments together; and FIGS. 15 through 21 are isometric views of embodiments of implants in un-flexed positions in accordance with the principles described herein.

DETAILED DESCRIPTION

Figure 1:
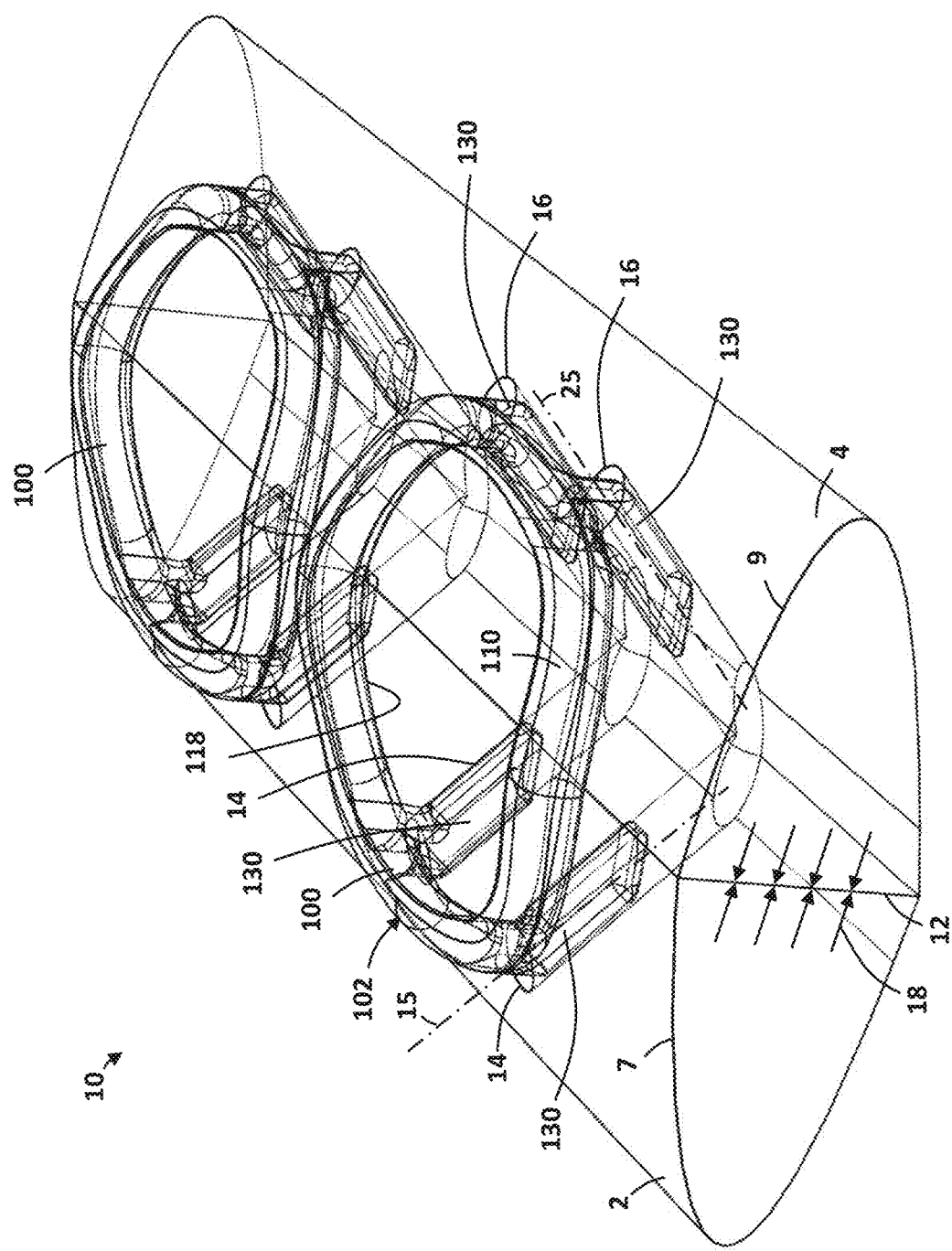
FIG. 1 is an isometric view of an embodiment of an implant for compressing two bone segments together in accordance with the principles described herein.

The following discussion is directed to various exemplary embodiments. However, one of ordinary skill in the art will understand that the examples disclosed herein have broad application, and that the discussion of any embodiment is meant only to be exemplary of that embodiment, and not intended to suggest that the scope of the disclosure, including the claims, is limited to that embodiment.

The drawing figures are not necessarily to scale. Certain features and components herein may be shown exaggerated in scale or in somewhat schematic form and some details of conventional elements may not be shown in interest of clarity and conciseness. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection of the two devices, or through an indirect connection that is established via other devices, components, nodes, and connections. In addition, as used herein, the terms "axial" and "axially" generally mean along or parallel to a given axis (e.g., central axis of a body or a port), while the terms "radial" and "radially" generally mean perpendicular to the given axis. For instance, an axial distance refers to a distance measured along or parallel to the axis, and a radial distance means a distance measured perpendicular to the axis. As used herein, the terms "approximately," "about," "substantially," and the like mean within 10% (i.e., plus or minus 10%) of the recited value. Thus, for example, a recited angle of "about 80°" refers to an angle ranging from 72° to 88°.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

As previously described above, staple-style orthopedic implants are designed to provide fixation and stability at a fracture, osteotomy or arthrodesis site to facilitate and enable fusion. Such implants may include 2, 3, 4 or more legs. The legs of the implant are connected with a bridge that may come in various forms, sizes, and shapes depending on the application and anatomy. The implants are usually part of system that includes instruments and a surgical technique. The instruments may include for example: sizing guides/templates, drill guides, drill or drilling pins, locating pins/pull pins, tamps, insertion tools, removal tools, and possibly heat source instruments for shape memory alloys.

There are generally three types of orthopedic staple-style implants (or more simply "orthopedic staples"): (1) static staples, (2) mechanical compression staples, and (3) shape memory compression staples. Static staples generally represent the first-generation orthopedic bone staples. These basic, U-shaped staples are typically made from medical grade titanium or stainless-steel materials suitable for medical device application. Traditional milling, wire-EDM, or wire-bending methods are usually employed to manufacture static staples. Static staples usually provide minimal to no compression to an osteotomy or arthrodesis site, and provide minimal stability to promote fusion at the site. Mechanical compression staples are typically manufactured from stainless steel materials. These staples rely on the application of an external force to achieve compression between bone fragments at an osteotomy or arthrodesis site. In particular, by physically bending the bridge with a suitable instrument, the distance between the implant legs is shortened, thereby allowing the legs to provide compression therebetween. Due to the limited elasticity of stainless steel, the compression provided is relatively short-lived. In addition, the deformation of the bridge may cause the tips of the implant legs to splay resulting in the distraction of the bone segments. Shape memory compression staples are often made from medical grade Nitinol suitable for medical device applications. Nitinol is a metal alloy made of approximately half nickel and half titanium. Nitinol exhibits phase transformation whereby the molecular arrangement of Nitinol can vary according to the temperatures to which it is exposed. At lower temperatures, the crystalline architecture of Nitinol resembles an accordion making it relatively unstable, malleable, and weak. This is referred to as the martensitic phase of Nitinol (martensite). At higher temperatures, the crystalline structure of Nitinol is rearranged into a cubic form making it contracted, rigid, and strong. This is referred to as the austenitic phase of Nitinol (austenite). The temperature range at which Nitinol transforms from the martensitic phase into austenitic phase can be adjusted and manipulated through manufacturing processes. During manufacturing, a Nitinol device undergoes heat treatments that "program" the temperature ranges that trigger the transition between the martensitic and austenitic phases. For example, when a Nitinol device is heated, the programing dictates the beginning of the phase transformation from martensite to austenite (Austenite Start temperature or $A_s$) and the end of the transformation (Austenite Finish temperature or $A_f$). In addition, when a Nitinol device is cooled, the programming dictates the beginning of the phase transformation from austenite to martensite (Martensite Start temperature or $M_s$) and the end of the transformation (Martensite Finish temperature or $M_f$). In addition to the aforementioned phase transformation, Nitinol exhibits shape memory and superelastic/pseudoelastic characteristics.

With regards to shape memory, a Nitinol device can be designed to transform from one shape to another when exposed to heat. For example, prior to heat treating, the Nitinol device may be cooled, and thus become malleable in the martensite material phase and shaped into a particular form that imparts internal residual stresses. Heat treatment can then be applied, which sets or "bakes" this established shape into the memory of the implant. Then, when the Nitinol device is heated through its transformation temperature range, the device will revert to its predetermined final shape as it undergoes the phase transformation to Austenite.

Compared to most other metals, Nitinol can withstand a large amount of strain, for example up to 8%, and still recover its original shape. The superelastic characteristic is displayed when a Nitinol staple is warmed through its transformation temperature range but is constrained and prevented from returning to its original shape. While constrained in a deformed shape, as is the case when a Nitinol bone staple is in bone, continuous exposure to sufficient heat allows the implant to behave like an elastic spring. This superelastic effect thus may be used to maintaining a long-term compressive force between bone segments over a large displacement range.

There are two varieties of staples are made from Nitinol: Thermally-activated and Superelastic. The transition temperature ranges of these types of implants vary and can be classified as either heat-activated or body temperature-activated. Heat-activated Nitinol bone staples have an $A_s$ and $A_f$ above body temperature. These implants are inserted into bone in the malleable martensitic phase and are exposed to an external heat via electrocautery or bi-polar electrical resistance to convert the implant from martensite to austenite, and thus, promote shape change that creates initial compression between joined bone segments. Compression is maintained through the superelastic effect as the implant is constrained in an open position by the bone segments. Body temperature-activated Nitinol bone staples have a transition temperature range that is slightly lower than body temperature. Since their austenite start temperature ($A_s$) may be at or below room temperature, these implants may utilize freezer storage to prevent premature closure. These implants are placed into the osteotomy or arthrodesis site while still in a frozen state, and then compress the joined bone segments through the shape memory effect as they warm to body temperature. Compression is again maintained through the superelastic effect as the implant is constrained in an open position by the bone segments. Both types of thermally-activated Nitinol implants (e.g., heat- and body temperature-activated) have not, however, been widely accepted. Due to manufacturing limitations of thermally-activated Nitinol, traditional machining methods (milling, grinding, turning, etc.) have generally not been cost-effective. Thus, many Nitinol staples are created using raw Nitinol wire material that is bent to the desired shape and heat treated to set the shape. This has generally limited implant geometries to simple U-shaped staples having two legs and a constant cross-section between the distal ends of the implant legs.

Superelastic shape memory compression staples are the latest generation of Nitinol bone implants. The austenite finish temperature ($A_f$) for these implants is significantly below room temperature, for example 10 to −20 degrees C., thus freezer storage to maintain an initial shape in the martensite material phase may not be sufficient, as implants may begin to deflect before being placed into the osteotomy or arthrodesis site. Thus, in some instances, external constraint devices may be used to mechanically open and constrain the legs of the implant prior to inserting them into pre-drilled holes in bone. Upon release of the constraining tool, the superelastic effect is transferred from the tool to the bone to achieve compression across the osteotomy or arthrodesis site.

Due to a relatively low $A_f$ (e.g., 10 to −20 degrees C.), superelastic Nitinol implants may utilize different manufacturing approaches as compared to implants made from wire raw material, and thus, may include more configurations and geometries, such as additional staple legs. For example, starting with bulk raw material with low $A_f$, implants may be machined using wire Electrical Discharge Machining (EDM) to create the desired shapes. The shapes of these implants are however limited to the shapes that may result from the intersection of wire paths from two planes, and thus, such implants may not conform to the complex anatomies of the body. Additionally, due to the EDM manufacturing process, the leg features typically have square or rectangular cross-sectional shapes that do not match the shape and size of the round drilled holes in which the legs are installed. A result of this mismatch is that the implant leg strength may not be maximized, and thus, the most common fracture location of a staple is in the leg features. This typically limits the use of staples to applications in lower biomechanical loading areas. However, as staples become more common practice for surgeons, there is a continued desire to use staples in high biomechanical loading applications.

Accordingly, embodiments disclosed herein include staple-style implants (which may be alternatively referred to herein as "implants," or "orthopedic implants," "staples," or "orthopedic staples") that may be produced with more complex geometries than what is typically possible with EDM machining. In particular, some embodiments disclosed herein may utilize advanced milling techniques and/or electrochemical machining (ECM) to produce implants having rounded or partially rounded legs and implant bridges that have different cross-sectional shapes than the corresponding legs. In addition, the implant bridges may be formed in numerous different configurations and may include a partially rounded profile that provides a low implant profile and establishes a more anatomically conforming fit that minimizes the overlying soft tissue irritation is some surgical applications. Also, embodiments disclosed herein include implants that store torsional stress along one or more portions thereof and/or a combination of torsional and bending stress, which allows the legs of the implant to be biased or "spring loaded" for enabling the application of compressional loads.

Referring now to FIG. 1, an embodiment of an implant 100 is shown. In this embodiment, implant 100 is an oval-shaped staple used to fix, stabilize, and apply compression (illustrated with arrows 18 in FIG. 1) across a fracture 12 between a first bone segment 2 and a second bone segment 4 of a broken bone. Each bone segment 2, 4 has a curved, convex outer surface or profile 7, 9, respectively, immediately adjacent implant 100. Bone segments 2, 4 represent an exemplary curved profile (e.g., round, elliptical, etc.) such as that of a sternum or breastbone as located on a patient's chest, however, as will be described more fully below, implant 100 may be used with any classification of bone (e.g., short, flat, sutural, irregular, sesamoid, long, etc.), and in locations with or without a curved profile. Although break 12 is shown generally along a plane oriented perpendicular to curved profiles 7, 9, in general, break 12 may be oriented at any angle with respect to curved profiles 7, 9.

In this embodiment, implant 100 includes a body 102 and a plurality of resilient legs 130 extending from and coupled to body 102. In this embodiments, the body 102 defines a resilient bridge 210 that extends across break 12, when implant 100 is secured to bone segments 2, 4 such that legs 130 penetrate into bone segments 2, 4 via corresponding holes 14, 16, respectively. In particular, a first plurality of holes 14 are drilled into first bone segment 2 and a second plurality of holes 16 are drilled into second bone segment 4. Each hole 14 has a linear central or longitudinal axis 15 and each hole 16 has a linear central or longitudinal axis 25 that is spaced apart from and oriented at an angle relative to each first axis 15. Thus, in this embodiment, holes 14 are not oriented parallel (or are non-parallel) to holes 16. However, in other embodiments, holes 14, 16 may be oriented parallel.

Legs 130 are pressed into and securely seated in holes 14, 16, and generally maintain a static, fixed position relative to corresponding bone segments 2, 4, as elastic energy stored within implant 100 applies compression 18 across the break 12. In some embodiments, an interference fit is provided between bone segments 2, 4 and legs 130 disposed in corresponding holes 14, 16. The angle between axes 15, 25 of the drilled holes 14, 16 may also contribute to the retention of implant 100. In particular, the angle between axes 15, 25 may in effect allow the plurality of legs 130 to capture portions of bone segments 2, 4 that are positioned between legs 130 and bridge 110, and compress such captured portions of bone segments 2, 4 between legs 130 and bridge 110, thereby further stabilizing break 12 against micro-motions that could slow or prevent healing or fusion of break 12.

Figure 2:
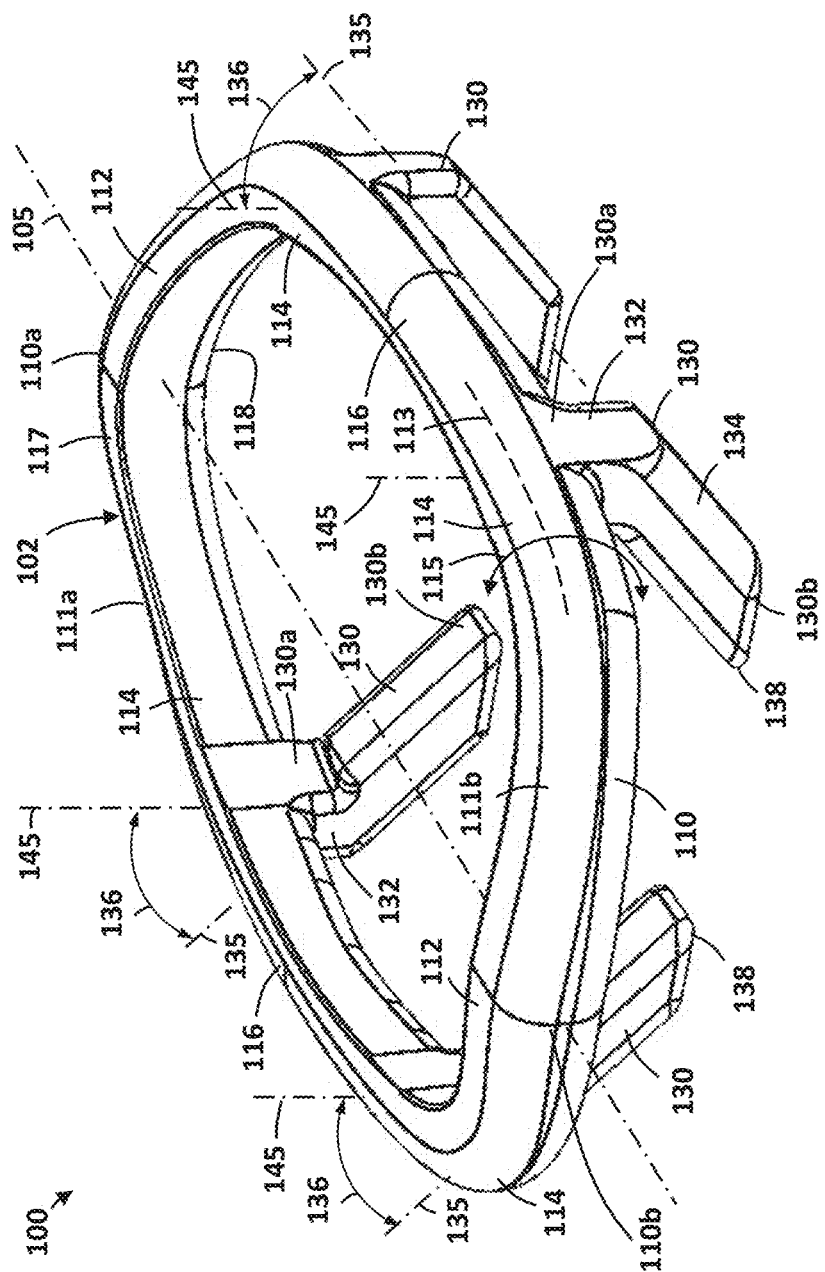
FIG. 2 is an isometric view of the implant of FIG. 1 in an un-flexed position.

Referring now to FIG. 2, implant 100 has a central or longitudinal axis 105 passing through a geometrical center of bridge 110 and centered between the pairs of opposed legs 130 in top view. In this embodiment, bridge 110 is formed as a closed loop that is generally circular in top view. In view of the foregoing, bridge 110 may be described as having axial ends 110a, 110b and two generally semi-circular sides 111a, 111b. Sides 111a, 111b are positioned on opposite sides of axis 105, and each side 111a, 111b extends circumferentially between ends 110a, 110b. In addition, bridge 110 has a first or upper surface 117 extending about the entire circumference bridge 110 and positioned distal bone segments 2, 4 when implant 100 is coupled thereto, and a second or lower surface 118 extending about the entire circumference bridge 110 and positioned proximal bone segments 2, 4 when implant 100 is coupled thereto. Legs 130 extend from lower surface 118. In particular, two legs 130 extend from lower surface 118 along each semi-circular side 111a, 111b of bridge 110 (i.e., on opposite sides of axis 105). The pair of legs 130 on each semi-circular side 111a, 111b of bridge 110 are circumferentially spaced with each leg 130 on semi-circular side 111a being radially or laterally opposed (relative to axis 105) one leg 130 on the opposite semi-circular side 111b.

The generally circular closed loop shape of bridge 110 may be divided into a plurality of circumferentially extending, arcuate regions or segments. In particular, bridge 110 includes a pair of arcuate shaped first regions 112 that span across central axis 105, a plurality of resilient torsion region 114 from which legs 130 extend, a pair of second regions 116 extending between torsion regions 114. Each first region 112 extends circumferentially between torsion regions 114 on opposite semi-circular sides of bridge 110, and each second region 116 extends between torsion regions 114 on the same semi-circular side of bridge 110. Thus, each first region 112 extends circumferentially into both sides 111a, 111b, and each side 111a, 111b includes two torsion regions 114 (one associated with each leg 130) and one second region 116 extending between the corresponding legs 130.

Referring still to FIG. 2, each leg 130 has a first or fixed end 130a fixably attached to and integral with a corresponding torsion region 114 of bridge 110 and a second or free end 130b distal bridge 110. In addition, each leg 130 has a first or upper leg portion 132 extending from fixed end 130a, a second or lower leg portion 134 extending from upper leg portion 132 to free end 130b, and a beveled tip 138 at free end 130b. Upper leg portion 132 has a central axis 145 and lower leg portion 134 has a central axis 135. In this embodiment, central axes 145 of upper leg portions 132 are oriented parallel to each other.

For each leg 130, axes 135, 145 intersect at the junction of portions 132, 134 and lie in a common plane oriented perpendicular to axis 105. In addition, for each leg 130, axes 135, 145 are oriented at a non-zero leg angle 136 measured between axes 135, 145 in the common plane within which they are disposed. In some embodiments, the leg angle 136 may comprise an acute angle. Accordingly, each leg 130 is bent at the intersection of upper leg portion 132 and lower leg portion 134, which may also be referred to herein as a "dog leg" along leg 130. In some embodiments, each leg angle 136 is greater than or equal to 0° and less than or equal to 90°, alternatively greater than or equal to 0° and less than or equal to 60°, alternatively greater than or equal to 0° and less than or equal to 45°, and alternatively greater than or equal to 0° and less than or equal to 30°. In this embodiment, each leg angle 136 is the same, and in particular, is about 45°. In other embodiments, one or more leg angles 136 may be different from one or more of the other leg angles 136. As shown in FIG. 2, the bent legs 130 and associated leg angles 136 between leg portions 132, 134 result in lower leg portions 134 generally sloping or tapering laterally inward toward central axis 105 in top view moving along lower leg portions 134 from corresponding upper leg portions 132 toward tips 138.

In this embodiment, implant 100 is made of a Nitinol material. Accordingly, implant 100 can be heat treated and programed, as discussed above, to have shape memory and superelastic/pseudoelastic characteristics such that implant 100 may be classified as a superelastic shape memory implant. For example, implant 100 may transform between two different configurations or positions when exposed to heat. In addition to or as an alternative, implant 100 can be resiliently flexed and elastically deformed via the application of external forces, and subsequently released (i.e., by removal of the external forces) to allow implant 100 to transform between two different configuration or positions.

Referring now to FIGS. 3 and 4, the surgical use of implant 100 may utilize and leverage the shape memory characteristics of Nitinol to impart compressive loads across a fracture, osteotomy or arthrodesis site (e.g., compression 18 across break 12) to facilitate and enable fusion. In the manner previously described, implant 100 can be made of Nitinol and programed through deformation and heat treatment, such that the shape memory of the Nitinol material increases the leg angles 136 (e.g., ends 130b move inwardly toward axis 105 in top view) and/or translates the lateral sides of bridge 110 on opposite sides of axis 105 in response to heating of implant 100. Such heating of implant 100 may be accomplished with an external source (e.g., heat-activated), or as implant 100 is brought to room temperature or body temperature (e.g., body temperature-activated). Accordingly, implant 100 can be programmed such that tips 138 are positioned to align with holes 14, 16, and then legs 130 can be advanced into holes 14, 16 as implant is heated to translate tips 138 laterally and radially inward relative to axis 105 in top view as legs 130 are advanced into holes 14, 16 until lower surface 114 of bridge 110 is pressed into contact (or approximate contact) with bone segments 2, 4 as the curvature of lower surface 118 of bridge 110 may be specifically designed and selected to accommodate the underlying curved profiles 7, 9 of bone segments 2, 4 to allow a low implant profile and establish an anatomically conforming fit. Holes 14, 16 can be positioned and oriented such that the heating of implant results in residual bending and torsional stress remaining in implant 100 after legs 130 are fully seated in holes 14, 16 to bias ends 130b of legs 130 on opposite sides 111a, 111b radially and laterally inward (relative to axis 105 in top view) toward each other, thereby enabling legs 130 to apply compression across break 12. In some embodiments, the shape transformation may have already occurred and an external tool may be used to restrain the elastic deformation of implant 100 and maintain bending and torsional stress in implant 100 that biases legs 130 radially and laterally inward relative to axis 105 in top view. For example, in some embodiments, the external tool may engage bridge 110 and/or legs 130, and apply forces to bridge 110 and/or legs 130 to elastically flex bridge 110 and/or legs 130 to move tips 138 radially or laterally outward relative to axis 105 in top view, thereby moving axes 145 toward (or substantially to) parallel orientations. Thus, in some embodiments, bridge 110 and/or legs 130 may be elastically flexed and then constrained with tips 138 spaced apart and axes 145 oriented substantially parallel to align tips 138 with the openings of corresponding holes 14, 16 in bone segments 2, 4 (as shown in FIG. 3), and then inserted into corresponding holes 14, 16. Next, the external tool may be removed, to release the strain energy of the elastically deformed implant 100 as legs 130 are advanced into holes 14, 16 and lower portions 134 are allowed to transition into coaxial alignment with holes 14, 16. Legs 130 may be advanced into holes 14, 16 until lower surface 114 of bridge 110 is pressed into contact (or approximate contact) with bone segments 2, 4 as the curvature of lower surface 118 of bridge 110 may be specifically designed and selected to accommodate the underlying curved profiles 7, 9 of bone segments 2, 4 to allow a low implant profile and establish an anatomically conforming fit. Holes 14, 16 can be positioned and oriented such that legs 130 can remain in an elastically and resiliently flexed position once fully seated in holes 14, 16 to apply compression across break 12 as legs 130 are biased inward toward central axis 105 in top view.

In the manners described, implant 100 may be described as having a first or flexed position with bridge 110 and/or legs 130 storing bending and/or torsional stress and free ends 130b of legs 130 biased radially and laterally inward toward central axis 105 in top view, and a second or relaxed position with bridge 110 and legs 130 generally free of bending and/or torsional stress. When implant 100 and legs 130 are in the flexed position(s), second ends 130b and tips 138 of legs 130 are biased inwardly toward each other as implant 100 and legs 130 seek to transition to the un-flexed position(s). For example, in FIG. 3, implant 100 is shown in a flexed position with legs 130 urged apart and in FIG. 2, implant 100 is shown in the un-flexed position. In FIG. 4, implant 100 has transitioned from the flexed position shown in FIG. 3 toward the un-flexed position but has not achieved the un-flexed position, and thus, legs 130 continue to be biased radially and laterally inwardly.

Referring to FIG. 3, implant 100 is shown in the flexed position with lower ends 130b urged laterally and radially outward such that axes 135 of lower leg portions 134 are approaching parallel orientations, and only tips 138 are inserted into corresponding holes 14, 16. Holes 14, 16 are drilled in bone segments 2, 4, respectively, on opposite sides of the break 12 and oriented at acute angles relative to a reference plane 155 that is centered between holes 14, 16 on opposite sides of the break 12. In this embodiment, each hole 14, 16 is oriented at the same acute angle relative to the reference plane 155. Before legs 130 are advanced into holes 14, 16, break 12 may include a relatively small gap or space between first bone segment 2 and second bone segment 4.

An insertion tool (not shown) may be used to apply forces to implant 100 to establish and maintain the flexed position shown in FIG. 3 as both bending and torsional stresses are stored within bridge 110. Bending stresses may also be stored in legs 130 depending on how the insertion tool (not shown) interfaces implant 100, bridge 110, and legs 130. The deflected shape of bridge 110 and lower surface 118 shown in FIG. 3 relative to surfaces 7 and 9 of FIG. 4, evidence the bending stresses stored within bridge 110 (e.g., sides 111a, 111b of bridge 110 are elastically flexed upwardly). In addition, torsional stresses are stored within at least torsion regions 114 of bridge 110 proximal legs 130. Accordingly, as used herein, the phrase "torsion region" is used to refer to a region or portion of a bridge of an implant that is configured to twist and experience torsional loads when leg(s) of the implant are rotated to transition from an unflexed position to a flexed position. Specifically, as shown in FIG. 2, each torsion region 114 may extend lengthwise (or longitudinally) along a center line or axis 113 (which therefore may comprise a longitudinal axis of torsion region 114). The centerline 113 is schematically depicted for one of the torsion regions 114 of the implant 100 in FIG. 2. When implant 100 is transitioned to the flexed position (FIG. 3), the legs 130 are rotated about the centerline 113 of the corresponding torsion regions 114, which thereby induces a torsion (or twist) int the torsion regions 114 about the corresponding centerlines 113. This torsion is depicted with the arrow 115 for one of the torsion regions 114 of implant 100 in FIG. 2. This torsion (e.g., arrow 115) about the centerline 113 is distinct from a bending stress in which the centerline (e.g., centerline 113) of a region or portion of implant is deflected or bent itself.

In at least some embodiments, axes 135 of lower leg portions 134 of two axially adjacent legs 130 on the same side 111a, 111b may remain oriented parallel to each other between the flexed position and the un-flexed position, and thus, second regions 116 of bridge 110 between such legs 130 may concurrently have little or no torsional or bending stresses while first regions 112 experience bending stresses (e.g., in which a centerline of the first regions is bent or deflected) and torsion regions 114 experience torsional stresses. During insertion of legs 130 of implant 100 onto holes 14, 16 at stages between the positions shown in FIGS. 3 and 4, the insertion tool (not shown) may gradually release the applied loads on implant 100 such that the ends 130b of legs are gradually directed along the corresponding holes 14, 16.

Referring now to FIG. 4, legs 130 are fully seated in holes 14, 16 with lower surface 118 of bridge 110 seated against bone segments 2, 4. Axes 135 of lower leg portions 134 are coaxially aligned with corresponding axes 15, 25 of holes 14, 16, and conforming contact (or proximate contact) is achieved between lower surface 118 and curved profiles 7, 9 of bone segments 2, 4. The specific curvature of bridge 110 and lower surface 118 may be selected to provide a low implant profile and established an anatomically conforming fit.

As shown in FIG. 4, each leg 130 is in a partially flexed position, thereby ensuring ends 130b (and corresponding legs 130) are biased laterally and radially inward (e.g., toward reference plane 155) and enabling legs 130 and implant 100 to apply compressive loads across break 12. At least one of the torsional stresses within torsion regions 114 or the bending stresses within first regions 112 are still present in the partially flexed position to allow the plurality of legs 130 to provide constant compression 18 to break 12. In other words, each leg 130 is generally biased inwards in the flexed position and partially flexed position, and seeks to return to the unflexed position.

Figure 5:
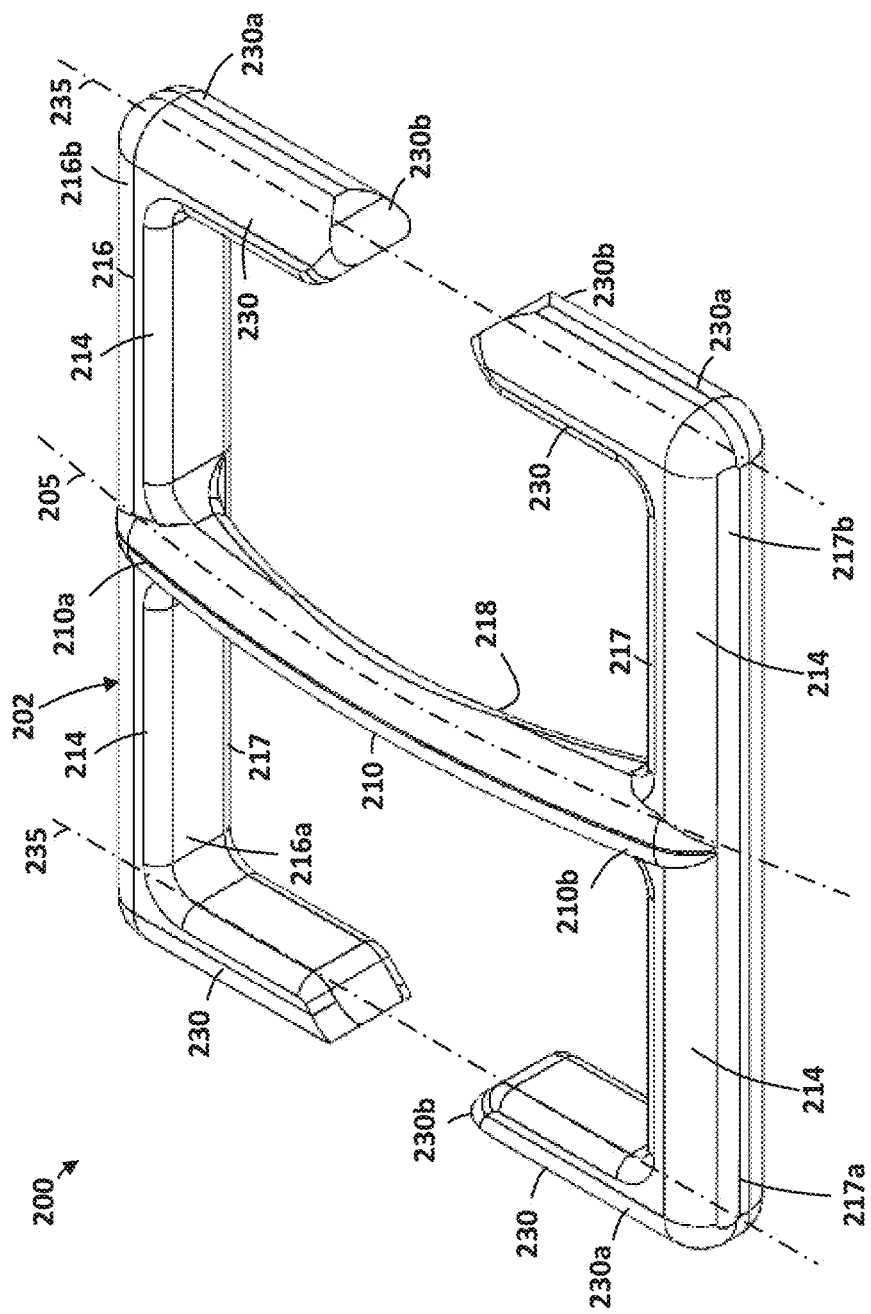
FIG. 5 is an isometric view of an embodiment of an implant in an un-flexed position in accordance with the principles described herein.

Referring now to FIG. 5, an embodiment of an implant 200 is shown. In general, implant 200 can be used in place of and exhibits similar functionality as implant 100 previously described. As shown in FIG. 5, rather than the generally circular closed loop shape of bridge 110 of implant 100 previously described, in this embodiment, implant 200 includes a body 202 comprising a single elongated resilient bridge 210 that spans between a first transversely oriented resilient member 216 and a second transversely oriented resilient member 217. Members 216, 217 are oriented perpendicular to bridge 210, and thus, body 202 is generally "H-shaped." Implant 200 has a central or longitudinal axis 205 passing through a geometrical center of bridge 210 and centered between the pairs of opposed legs 230 in top view.

Bridge 210 has a first axial end 210a and a second axial end 210b opposite first end 210a. End 210a is fixably attached to first member 216 and end 210b is fixably attached to second member 217. In this embodiment, ends 210a, 210b are fixably attached to members 216, 217, respectively, at the mid-length region of members 216, 217, respectively. First member 216 has ends 216a, 216b disposed on opposite sides of end 210a of bridge 210, and second member 217 has ends 217a, 217b disposed on opposite sides of end 210b of bridge 210. Thus, each member 216, 217 may be described as including a pair of resilient torsion regions 214, where each torsion region 214 extends from the corresponding end 210a, 210b of bridge 210 to the corresponding end 216a, 216b, 217a, 217b. One resilient leg 230 extends from each end 216a, 216b, 217a, 217b. Legs 230 extending from end 216a, 217a generally extend toward each other, and legs 230 extending from ends 216b, 217b generally extend toward each other in top view.

Referring still to FIG. 5, each leg 230 has a central or longitudinal axis 235 laterally spaced from and oriented generally parallel to axis 215 in top view, a first or fixed end 230a fixably attached to and integral with the corresponding end 216a, 216b, 217a, 217b of the corresponding member 216, 217, and a second or free end 230b distal the corresponding member 216, 217. As will be described in more detail below, implant 200 and legs 230 transition between a first or un-flexed position and a second or flexed position. In the un-flexed position shown in FIGS. 5 and 6A, each leg 230 is coaxially aligned with and extends towards an opposing leg 230 on the opposite member 216, 217. Namely, legs 230 extending from ends 216a, 217a are coaxially aligned, and legs 230 extending from ends 216b, 217b are coaxially aligned. In addition, in this embodiment, central axes 235 of legs 230 are disposed in a common reference plane in the un-flexed position. In the flexed position shown in FIG. 6B, no two legs 230 is coaxially aligned, however, central axes 235 of legs 230 extending from ends 216a, 217a are disposed in a first reference plane oriented parallel to axis 205 and perpendicular to the central axes of members 216, 217, and legs 230 extending from ends 216b, 217b are disposed in a second refence plane oriented parallel to axis 205 and perpendicular to the central axes of members 216, 217. Thus, the first reference plane is oriented parallel to the second reference plane.

Referring now to FIGS. 6A and 6B, similar to implant 100 previously described, implant 200 is configured to store torsional and/or bending stresses upon exposure to heat when implant 200 is heat treated and programed (e.g., to have shape memory and superelastic/pseudoelastic characteristics) and/or when elastically flexed from a first or un-flexed position (shown in FIG. 6A) to a second or flexed position shown in FIG. 6B. Implant 200 is shown transitioning from the un-flexed position in FIG. 6A to the flexed position in FIG. 6B as forces are imparted to implant 200 with an insertion tool (not shown). Unless otherwise restricted from doing so, implant 200 can transition from the flexed position in FIG. 6B to the un-flexed position in FIG. 6A by removal of such imparted forces. As will be described in more detail below, implant 200 and in particular legs 230 are generally biased to the unflexed position.

Bridge 210 is configured to store bending stresses as shown by displacement 224 (e.g., by flexing ends 210a, 210b upward), while torsion regions 214 of members 216, 217 are configured to store torsional stresses as shown by torsional displacements 222 about the centerlines (not shown) of the torsion regions 214 (e.g., by angular displacements 220 of legs 230 about the central axis of the corresponding member 216, 217 and within the corresponding first or second reference plane relative to the un-flexed positions). In some embodiments, the angular displacement 220 of each leg 230 relative to the un-flexed position ranges from about 10° to 180°, alternatively from about 10° to 120°, and from about 30° to 45°.

In some embodiments, the angular displacements 220 may be sufficient (e.g., 90°) to orient axes 235 parallel to each other such that legs 230 of implant 200 may be inserted into corresponding parallel drilled holes 14, 16. In such embodiments, the insertion tool (not shown) may hold legs 230 in parallel orientations as legs 230 are advanced into holes 14, 16 without gradually releasing the forces applied by the insertion tool to maintain implant 200 in the flexed position.

Referring now to FIG. 7, implant 200 is shown with legs 230 fully seated in holes 14, 16 and bridge 210 seated against bone segments 2, 4 in the flexed position (or partially flexed position), thereby enabling implant 200 to impart compressive loads across a fracture, osteotomy or arthrodesis site (e.g., compression 18 across break 12). After installation of implant 200 and release of the forces applied by the insertion tool, torsional stress in torsion regions 214 and/or bending stresses in bridge 210 bias legs 230 in directions 221 to the un-flexed positions. Thus, directions 221 are oriented directly opposite the corresponding directions of angular displacements 220, while displacement 224 of bridge 210 and torsional displacements 222 of torsion regions 214 are also oriented in the opposite directions in FIG. 7 as compared to those shown in FIG. 6. The partially flexed position and the flexed position may be substantially equivalent in this embodiment where holes 14, 16 are parallel as the initial position of bone segments 2, 4 may constrain angular directions 221 of legs 230.

Figure 8:
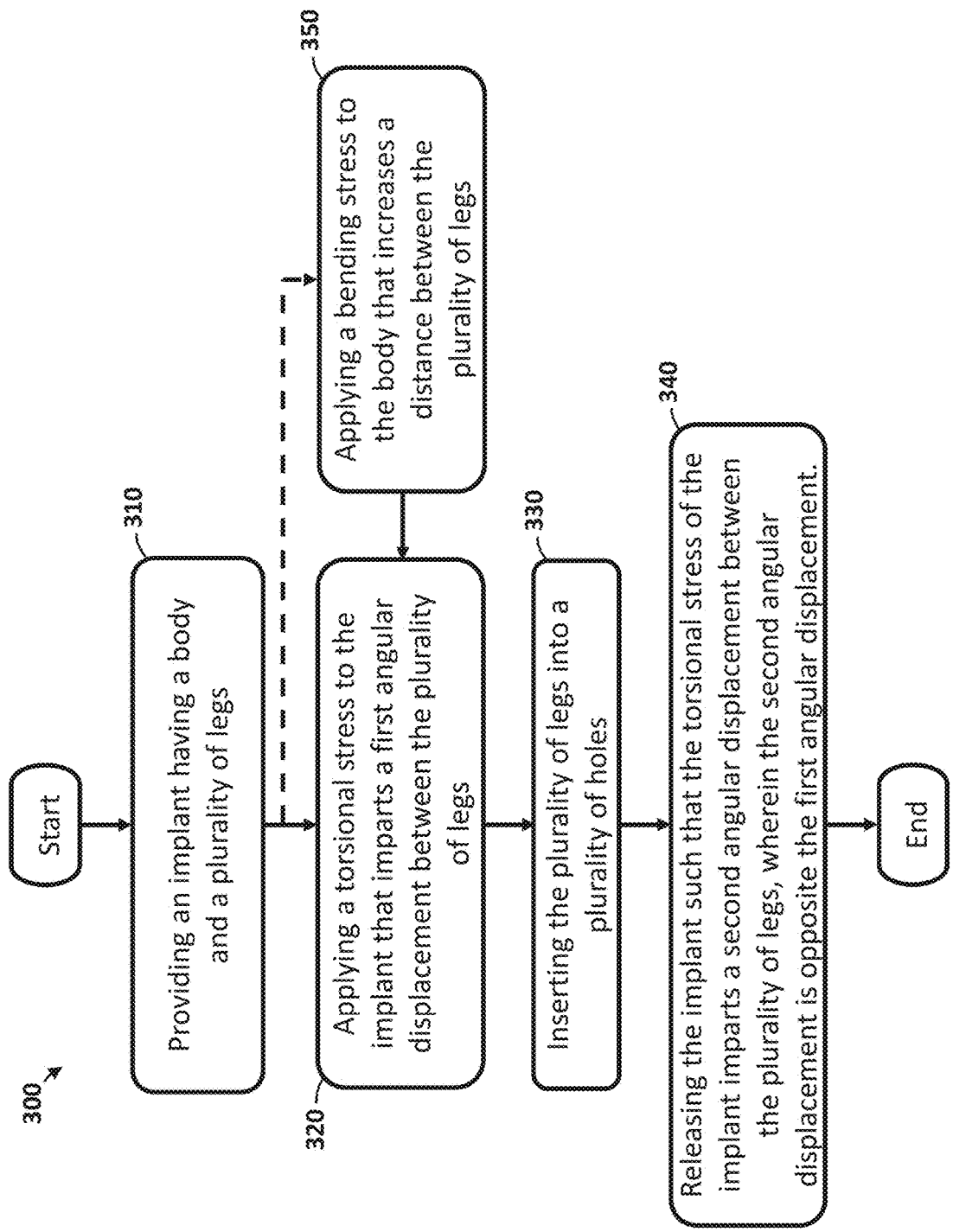
FIG. 8 is an embodiment of a method for installing implants in accordance with principles described herein.

Referring to FIG. 8, an embodiment of a method 300 for installing an implant (e.g., such as implants 100, 200 previously described) is shown. For convenience, FIG. 8 will be described in connection with FIGS. 6A, 6B, and 7 illustrating implant 200, however, method 300 is generally applicable to all the embodiments of implants disclosed herein. In FIG. 8, method 300 begins at block 310, by providing an implant 200 having a body 202 and a plurality of legs 230. Next, at block 320 torsional stress(es) are applied to the implant 200 (e.g., at the torsion regions 214 of body 202) to impart the angular displacements 220 to the plurality of legs 230. In some embodiments, torsional stresses result from externally applied forces of an insertion tool (not shown) that transitions the implant 200 from the un-flexed position to the flexed position as illustrated in FIGS. 6A and 6B, respectively. Moving now to block 330, the plurality of legs 230 are inserting into a plurality of holes 14, 16 in the bone segments 2, 4 as shown in FIG. 7. Then, in block 340, the insertion tool may release the implant 200 such that the torsional stresses in implant 200 (e.g., such as the torsional stress stored in torsion regions 214) bias the plurality of legs 230 in angular directions 221 to the un-flexed position, wherein the angular directions 221 are opposite the angular displacement 220. Block 350 may optionally also be used to apply a bending stress to the bridge 210 that increases a distance between the plurality of legs 230. In some embodiments, Block 350 may be performed before, after, or simultaneously with Block 320. Referring again to FIGS. 6 and 7, the bending stress applied to the body 202 (e.g., specifically bridge 210), as evidenced by displacement 224, may be a resultant stress from the torsional displacements 222 imparted along torsion regions 214 and/or may comprise a bending stress that is separately imparted by the insertion tool. For example, in some embodiments, the insertion tool may be configured to apply forces to a middle portion of bridge 210 and to ends 210a, 210b (e.g., 3-point bending) while also imparting the first angular displacement 220 to legs 230 that transfers a concentrated bending moments to ends 210a, 210b, and further, contributes to the bending of bridge 210.

Figure 9:
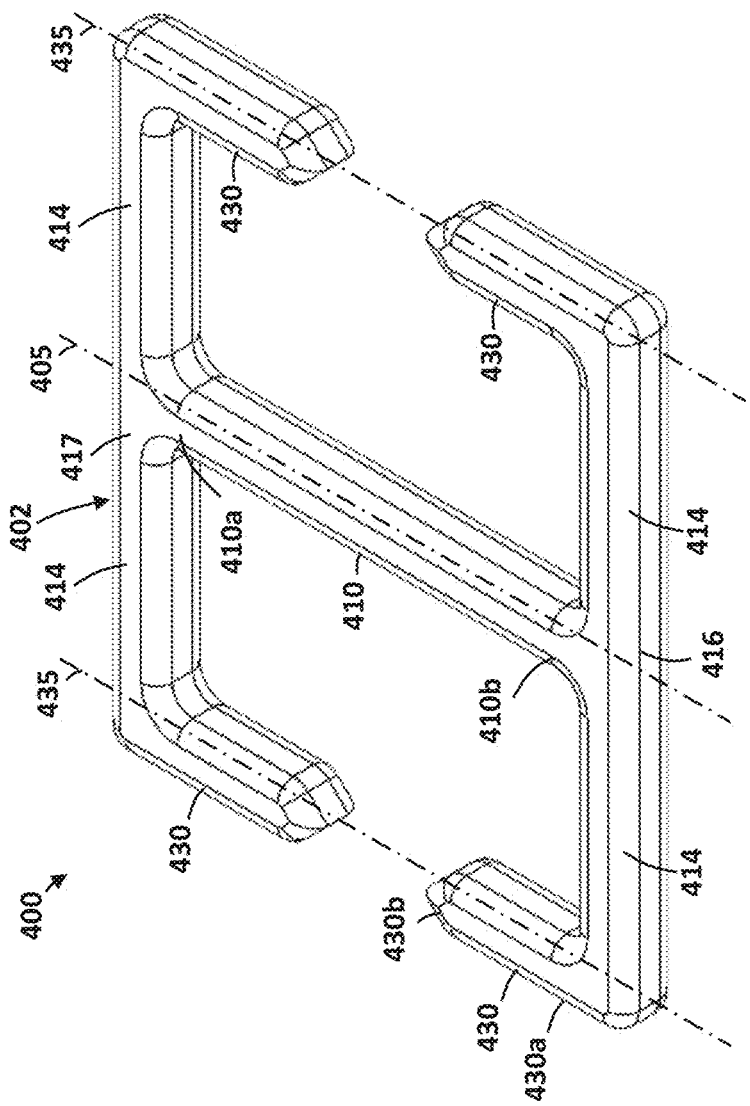
FIG. 9 is an isometric view of an embodiment of an implant in an un-flexed position in accordance with the principles described herein.

Referring now to FIG. 9, an embodiment of an implant 400 is shown. In general, implant 400 can be used in place of and exhibits similar functionality as implant 100 previously described and shown in FIG. 1. Similar to implant 200, implant 400 comprises an H-shaped body 402 that includes a single elongated resilient bridge 410 extending between a first transversely oriented resilient member 416 and a second transversely oriented resilient member 417. One member 416, 417 is attached to each end 410a, 410b of bridge 410. One resilient leg 430 extends from each end of each member 416, 417. Implant 400 has a central or longitudinal axis 405 passing through a geometrical center of bridge 410 and centered between the pairs of opposed legs 430 in top view.

In this embodiment, each leg 430 has a central axis 435, a first or fixed end 430a fixably coupled to an end of the corresponding member 416, 417, and a second or free end 430b distal the corresponding member 416, 417. As shown in FIG. 9, in this embodiment, opposed legs 430 extending from different members 416, 417 are coaxially aligned in the un-flexed position. In addition, in this embodiment, axes 435 and central axis 405 are disposed in a common reference plane in the un-flexed position. Each member 416, 417 may be described as including a pair of resilient torsion regions 414, where each torsion region 414 is coupled to a corresponding one of the legs 430 and is configured to experience torsional stresses (e.g., about a centerline thereof as previously described) when the legs 430 are transitioned to a flexed position.

Bridge 410 differs from bridge 210 (as best shown in FIG. 5) as bridge 410 has a uniform and constant cross-sectional geometry and area between ends 410a, 410b, while bridge 210 has a variable cross-sectional geometry and area between ends 210a, 210b. More specifically, bridge 210 of implant 200 includes a second or lower surface 218, which in some embodiments may be formed as an arc to provide an anatomically conforming fit with curved bone segments 2, 4. In particular, lower surface 218 is concave between ends 210a, 210b in side view. In general, the shape of lower surface 218 may be adjusted for any anatomical site and may include shapes other than a concave arc. In addition, the cross-sectional area of the bridge 210 may also be increased in the center of bridge 210 by varying one or more dimensions of the cross-section. For example, as previously described, an insertion tool may be used to impart a 3-point bend to bridge 210, and thus, regions of higher section modulus (e.g., higher bending strength) may be needed along central portions of bridge 210 to resist the maximum moment at the central position of bridge 210.

Figure 11:
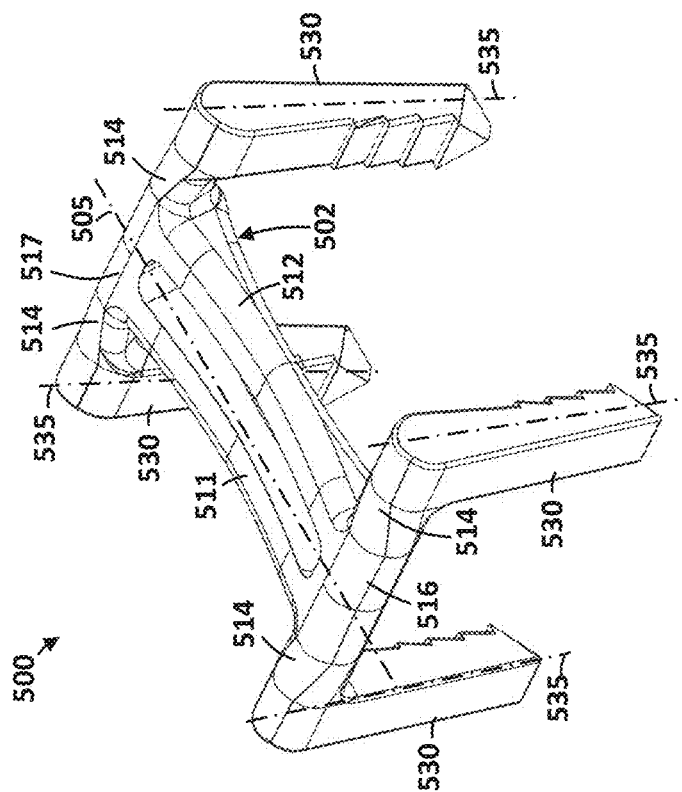
FIG. 11 is an isometric view of the implant of FIG. 10 in a flexed position.
Figure 10:
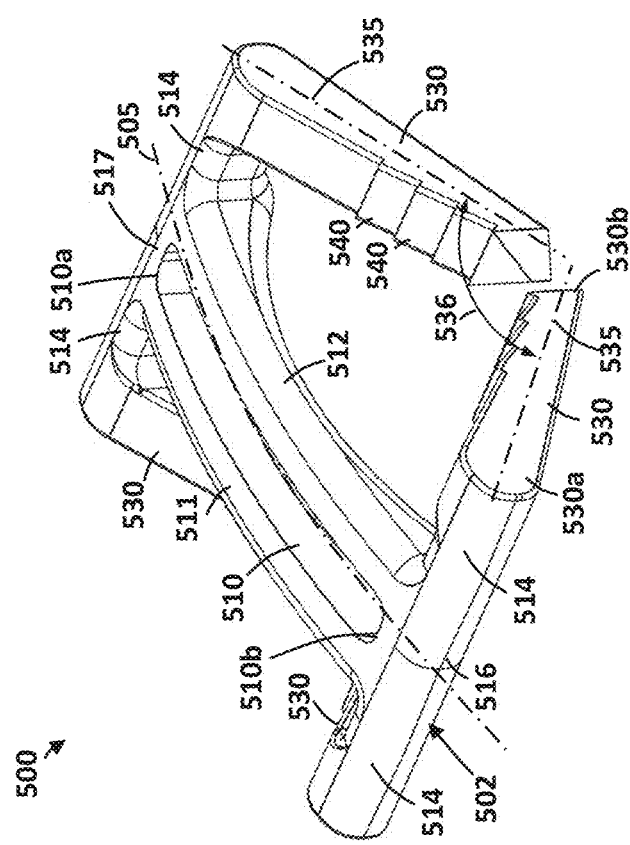
FIG. 10 is an isometric view of an embodiment of an implant in an un-flexed position in accordance with the principles described herein.

Referring now to FIGS. 10 and 11, an embodiment of an implant 500 is shown. In general, implant 500 can be used in place of and exhibits similar functionality as implant 200 previously described and shown in FIG. 1. Similar to implant 200, implant 500 comprises an H-shaped body 502 including an elongated resilient bridge 510 that spans between a first transverse resilient member 516 and a second transverse resilient member 517. Implant 500 has a central or longitudinal axis 505 passing through a geometrical center of bridge 510 and centered between pairs of opposed legs 530 in top view. One member 516, 517 is attached to each axial end 510a, 510b of bridge 510. However, rather than the singular elongated member that defines bridge 210 of implant 200, in this embodiment, bridge 510 of implant 500 includes two parallel elongated members that are laterally spaced apart relative to a central axis 505 of bridge 510. In addition, implant 500 differs from implant 200 in that implant 500 includes a plurality of serrations 540 distributed along each of the plurality of resilient legs 530, and no two legs 530 are coaxially aligned with implant 500 and legs 530 in the un-flexed position as shown in FIG. 10.

Referring to FIG. 10, bridge 510 includes a first elongate portion 511 extending from end 510a to end 510b and a second elongate portion 512 extending from end 510a to end 510b. Portions 511, 512 are laterally spaced apart relative to axis 505 and oriented parallel to axis 505. Both portions 511, 512 are fixably attached to the middle of first member 516 at end 510a, and portions 511, 512 are fixably attached to the middle of second member 517 at end 510b. Members 516, 517 are oriented perpendicular to axis 505 and portions 511, 512. A leg 530 extends from each end of each member 516, 517 at positions laterally spaced apart from central axis 505. Each leg 530 has a central or longitudinal axis 535, a first or fixed end 530a fixably attached to and integral with the end of the corresponding member 516, 517, and a second or free end 530b distal the corresponding member 516, 517. Central axes 535 of two opposed legs 530 extending from members 516, 517 lie in a first reference plane, and central axes 535 of two opposed legs 530 extending from members 516, 517 are disposed in a second reference plane. A leg angle 536 is measured in each reference plane between axes 535 of the opposed legs 530 in the corresponding reference plane. In this embodiment of implant 500, the leg angle 536 between each pair of opposed legs 530 is non-zero when implant 500 and legs 530 are in the un-flexed position. For most applications, each leg angle 536 ranges from about 0° to 90° when implant 500 and legs 530 are in the un-flexed position, alternatively ranges from about 0° to 60° when implant 500 and legs 530 are in the un-flexed position, alternatively ranges from about 0° to 45° when implant 500 and legs 530 are in the un-flexed position, and alternatively ranges from about 0° to 30° when implant 500 and legs 530 are in the un-flexed position. The portions of members 516, 517 extending between bridge 510 and legs 530 define resilient torsion regions 514 that are configured to experience torsional stresses (e.g., about a centerline thereof as previously described) when the legs 530 are transitioned to the flexed position.

Similar to implant 200 previously described, implant 500 is configured to store torsional and/or bending stresses (e.g., at the torsion regions 514 and/or along bridge 510, respectively) upon exposure to heat when implant 200 is heat treated and programed (e.g., to have shape memory and superelastic/pseudoelastic characteristics) and/or when elastically flexed from a first or un-flexed position (as shown in FIG. 10) to a second or flexed position (as shown in FIG. 11). In some embodiments, axes 535 of legs 530 are oriented parallel to teach other with implant 500 in the flexed position.

Figure 12:
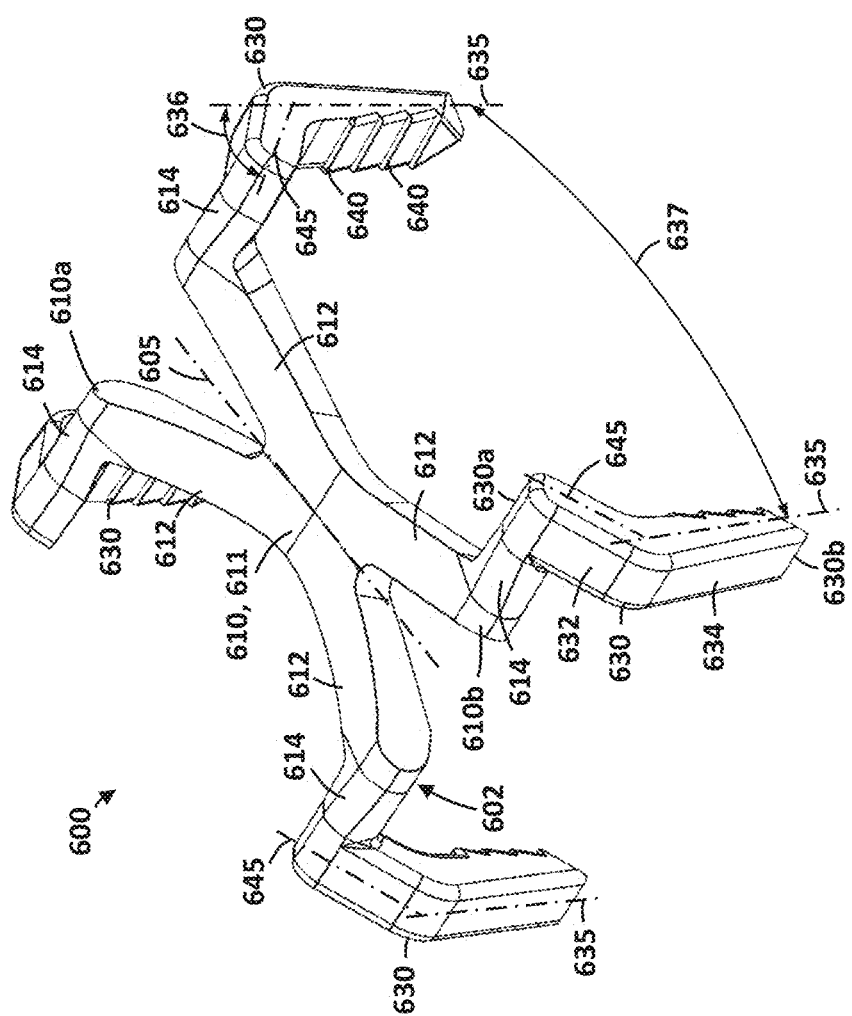
FIG. 12 is an isometric view of an embodiment of an implant in a flexed position in accordance with the principles described herein.

Referring to FIG. 12, an embodiment of an implant 600 is shown in a flexed position. In general, implant 600 can be used in place of and exhibits similar functionality as implant 100 previously described and shown in FIG. 1. Unlike implants 200, 400, 500 previously described that included H-shaped bodies 202, 402, 502, respectively, in this embodiment, implant 600 comprises an "X-shaped" body 602. In particular, body 602 includes a resilient bridge 610 and with a plurality of resilient torsion regions 614 that are coupled to bridge 610. In addition, implant 600 comprises a plurality of resilient legs 630 that are coupled to body 602 via the plurality of torsion regions 614. Implant 600 has a central or longitudinal axis 605 passing through a geometrical center of bridge 610 and centered between the pairs of opposed legs 630 in top view. Bridge 610 has a first axial end 610a and a second axial end 610b opposite first end 610a. In addition, bridge 610 includes a central portion 611 axially disposed between ends 610a, 610b, a first pair of extensions 612 extending axially from central portion 611 to end 610a, and a second pair of extensions 612 extending axially from central portion to end 610b. Thus, the first pair of extensions 612 and the second pair of extensions 612 extend axially in opposite directions from central portion 611. The first pair of extensions 612 generally diverge moving axially from central portion 611 to end 610a, and the second pair of extensions 612 generally diverge moving axially from central portion 611 to end 610b. In this embodiment, each extension 612 is oriented at an acute angle relative to central axis 605 in top view, and in particular, each extension 612 is oriented at the same acute angle relative to central axis 605 in top view.

At ends 610a, 610b, one resilient torsion region 614 extends laterally outward (relative to central axis) from each extension 612, and one resilient leg 630 extends from the distal end of each torsion region 614. In particular, each leg 630 has a first or upper end 630a, a second or lower end 630b, an upper leg portion 632 extending from upper end 630a, and a lower leg portion 634 extending from upper leg portion 632 to lower end 630b. Upper leg portion 632 of each leg 630 has a central axis 645 and lower leg portion 634 of each leg 630 has a central axis 635. Axes 635, 645 of each leg 630 are oriented at a non-zero leg angle 636 (that may comprise an acute angle in some embodiments) measured between axes 635, 645 in a reference plane containing both axes 635, 645, thereby defining a bent profile or dog leg between upper leg portion 632 and lower leg portion 634. Upper end 630a of each leg 630 is fixably attached to the distal end of one torsion region 614, and lower end 630b of each leg 630 is distal the corresponding torsion region 614 and bridge 610. In this embodiment, each leg angle 636 is the same, however, in other embodiments, each leg 630 may include a different leg angle 636 and/or one or more leg angles 636 may be zero such that upper leg portion 632 and lower leg portion 634 are collinear. For most applications, the leg angle 636 ranges from about 0° to 90°, alternatively from about 0° to 60°, alternatively from about 0° to 45°, and alternatively from about 0° to 30°.

Similar to implant 500 shown in FIG. 10, axes 635 of opposing pairs of legs 630 coupled to opposite ends 610a, 610b may be oriented at a leg angle 637 measured between axes 635 in a plane containing both axes 635 when implant 600 is in the un-flexed position. Leg angle 637 may range from about 0° to 90°, alternatively from about 0° to 60°, alternatively from about 0° to 45°, and alternatively from about 0° to 30°.

In some embodiments, a plurality of serrations 640 are provided on lower portion 634 of each leg 630 along the inner opposing surfaces, and thus, between opposing surfaces of legs 630 that are torsionally biased inward together as implant 600 moves from a flexed position to an un-flexed position.

Similar to implant 200 previously described, implant 600 is configured to store torsional and/or bending stresses (e.g., at the torsion regions 614 and/or along bridge 610, respectively) upon exposure to heat when implant 600 is heat treated and programed (e.g., to have shape memory and superelastic/pseudoelastic characteristics) and/or when elastically flexed from a first or un-flexed position to a second or flexed position (as shown in FIG. 12). In some embodiments, axes 635 of lower leg portions 634 are oriented parallel to each other with implant 600 in the flexed position.

Referring now to FIGS. 13 and 14, an exemplary surgical use of implant 600 is shown in connection with bone segments 2, 4, which have nominally flat upper surfaces and a plurality of holes 14, 16 drilled oversized to accommodate the bend in each leg 630 (i.e., the dog leg shape between upper leg portion 632 and lower leg portion 634). FIG. 13 illustrates implant 600 in the flexed position with axes 635 of legs 630 approaching parallel orientations and lower ends 630b of legs 630 inserted into corresponding holes 14, 16. In this condition, break 12 between bone segments 2, 4 may include a small gap or space segments 2, 4. Holes 14, 16 are drilled in bone segments 2, 4, respectively, on opposite sides of the break 12 and oriented at acute angles relative to a reference plane 655 that is centered between holes 14, 16 on opposite sides of the break 12. In this embodiment, each hole 14, 16 is oriented at the same acute angle relative to the reference plane 655. In other embodiments, holes 14, 16 may be drilled parallel or at an obtuse angle relative to reference plane 655.

As previously described, an insertion tool (not shown) may be used to apply forces to implant 600 to establish and maintain the flexed position as bending stresses and/or torsional stresses are stored within legs 630, bridge 610, torsion regions 614, or combinations thereof. The bending stresses and/or torsional stresses bias lower ends 630b of opposed legs 630 coupled to opposite ends 610a, 610b toward each other in a similar manner as implants 100, 200, 400, 500 previously described.

In some embodiments, such as the embodiment of FIG. 13, serrations 640 of opposing legs are initially disengaged from contact with the inner diameters of holes 14, 16 which are drilled larger than lower leg portion 634. In other words, the diameters of holes 14, 16 are greater than the maximum width or diameter of lower leg portions 634.

During insertion of implant 600 at stages between the positions shown in FIGS. 13 and 14, the insertion tool (not shown) gradually release the applied loads on implant 600 such that the ends 630b of legs are gradually directed along the corresponding holes 14, 16.

Referring now to FIG. 14, implant 600 is fully seated against bone segments 2, 4 and is in a partially flexed position as implant 600 imparts compressive loads across a fracture, osteotomy or arthrodesis site (e.g., compression 18 across break 12). The torsional stresses within torsion regions 614, the bending stresses within bridge 610, the bending stresses within legs 630, or combinations thereof are still present in the partially flexed position, thereby biasing implant 600 and legs 630 to the unflexed position as the plurality of legs 630 provides constant compression 18 to break 12.

As shown in FIG. 14, bridge 610 may not conform to the curvature of bone segments 2, 4 in some embodiments. In addition, the bent dog leg shape of legs 630 may establish a wedging fit within holes 14, 16 which offers the potential to aid in the retention and fixation stability of implant 600. In particular, in some embodiments the bent transition between the upper leg portion 632 and the lower portion 634 may contact the inner surfaces of bone segments 2, 4 defining holes 14, 16 to provide a bending fulcrum that biases legs 630 toward reference plane 655. As a result, serrations 640 of opposing legs 630 may be pressed into engagement with bone segments 2, 4 as the above described bending and torsional stresses of implant 600 rotate and/or translate legs 630. It is anticipated that such configurations may be particularly advantageous for applications where implant 600 is only temporarily implanted in a patient or where revision surgeries are anticipated. In particular, bone remodeling around legs 630 may take longer considering holes 14, 16 may be drilled oversized as compared to the size of legs 630. Thus, the surgical insertion tool which was used to place implant 600, or another tool (neither shown), could be used to reapply bending and/or torsional stresses to implant 600 to rotate legs 630 about the fulcrum interface described above to disengage serrations 640 from bone segments 2, 4, and generally release legs 630 from holes 14, 16.

It is anticipated that various design features previously described for implants 100, 200, 400, 500, 600 may be combined in numerous combinations without departing from the principles disclosed herein. For example, the shape of the bridge and legs may be adjusted to accommodate specific anatomical features, and to account for the magnitude and direction of biomechanical loads at each surgical location. In addition, the axial length and/or lateral width of the bridge may be increased to provide greater distances between the legs coupled to opposite end of the bridge and/or greater distances between the legs coupled to the same end of the bridge, while also decreasing the effective stiffness of the bridge to allow increased elastic deflections as the bridge is stressed under bending and/or torsional loads. For instance, with respect to implant 200 shown in FIGS. 6A, 6B, and 7, increased lengths of torsion regions 214 may allow larger angular displacements 220, while also reducing the magnitude of compression 18 for a given angular displacement 220. Alternatively, larger cross-sections along portions of the bridge and/or legs may increase the effective stiffness of the implant, and thus, may reduce the allowable elastic deflections and/or increase the magnitude of compressional loads (e.g., compression 18). Portions of the bridge and/or legs may be preferentially expanded or reduced to manage (e.g., reduce) the maximum stresses therein, and the dimensions of the bridge and/or legs may be selected to ensure there is no plastic deformation of the implant when transitioned between the un-flexed position and the flexed position. Thus, the dimensions and features of implants 100, 200, 400, 500, 600 may be combined and adjusted to balance the proportion of bending stresses and torsional stresses imparted, adapt to patient specific anatomy, react to the unique biomechanical loads at different surgical locations, and provide secure fixation and stability at a fracture, osteotomy or arthrodesis site while applying compression to enable fusion.

Referring generally to FIGS. 15 through 21, embodiments of implants 700, 800, 900, 1000, 1100, 1200, 1300 are presented to illustrate various combinations of features that may be selected from implants 100, 200, 400, 500, 600 to tailor the implant for a particular surgical location, as well as to illustrate features not previously disclosed. In general, implants 700, 800, 900, 1000, 1100, 1200, 1300 can be used in place of and offer similar functionality as implants 100, 200, 400, 500, 600 previously described.

Figure 15:
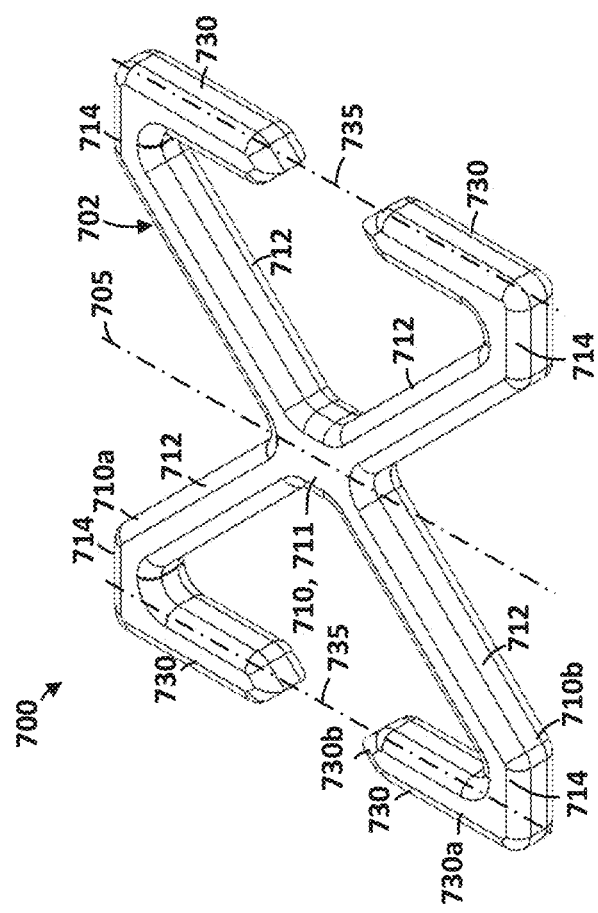

Referring first to FIG. 15, similar to implant 600 previously described, implant 700 comprises an X-shaped body 702 that includes a resilient bridge 710 and a plurality of resilient torsion regions 714 coupled to bridge 710, and a plurality of resilient legs 730 coupled to body 702 (and thus bridge 710) via torsion regions 714. Implant 700 has a central or longitudinal axis 705 passing through a geometrical center of bridge 710 and centered between the pairs of opposed legs 730 in top view. Bridge 710 has a first axial end 710a and a second axial end 710b opposite end 710a. In addition, bridge 710 includes aa central region 711, a first pair of extensions 712 extending axially from central region 711 to end 710a, and a second pair of extensions 712 extending axially from central region 711 to end 710b. The first pair of extensions 712 diverge moving axially from central region 711 to end 710a, and the second pair of extensions 712 diverge moving axially from central region 711 to end 710b. One torsion region 714 extends laterally from the distal end of each extension 712, and one leg 730 extends from the distal end of each torsion region 714. Each leg 730 has a central or longitudinal axis 735, a first or fixed end 730a fixably coupled to and integral with the distal end of one torsion region 714, and a second or free end 730b distal torsion regions 714.

Unlike implant 600 shown in FIG. 12, implant 700 does not include a bend or dog leg shape along each leg 730. Rather, in this embodiment, legs 730 are oriented configured the same legs 230 of implant 200 shown in FIG. 5. In particular, central axes 735 of legs 730 are spaced apart from and parallel to central axis 705 of bridge 710 in the un-flexed position. In addition, axes 735 of opposed legs 730 coupled to opposite ends 710a, 710b of bridge are coaxially aligned in the un-flexed position. Still further, in this embodiment, axes 735 and central axis 705 are disposed in a common reference plane in the un-flexed position.

Figure 16:
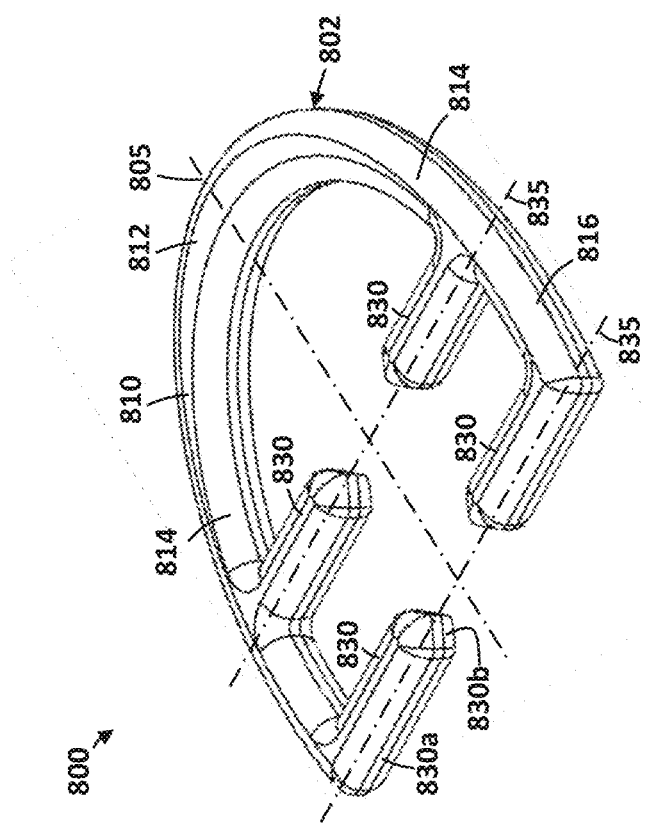

Referring to FIG. 16, similar to implant 100 previously described, implant 800 comprises a "rounded-shape" body 802 that defines a semi-circular or U-shaped of resilient bridge 810 and a plurality of circumferentially-spaced resilient legs 830 coupled to bridge 810. However, unlike implant 100 shown in FIG. 2, bridge 810 of implant 800 is not completely closed, but rather, only forms a partial circle or oval. Implant 800 has a central or longitudinal axis 805 passing through a geometrical center of bridge 810 and centered between the pairs of opposed legs 830 in top view. Bridge 810 has a first axial end 810a and a second axial end 810b opposite end 810a. In addition, bridge 810 includes a semi-circular arcuate shaped region 812 centered relative to central axis 805, a pair of torsion regions 814 extending from arcuate shaped region 812, and pair of distal regions 816 extending from torsion regions 814. In particular, arcuate-shaped region 812 extends from and defines end 810a, distal regions 816 extend from and define end 810b, and torsion regions 814 are disposed between arcuate-shaped region 812 and distal regions 816. A pair of axially-spaced legs 830 extend laterally inward from each distal region 816. Each leg 830 has a central or longitudinal axis 835, a first or fixed end 830a fixably coupled to and integral with one torsion region 814, and a second or free end 830b distal the corresponding torsion region 814. In this embodiment, central axes 835 and central axis 805 are disposed in a common reference plane in the un-flexed position.

In addition to bridge 810 not being a closed loop structure like bridge 110, other differences between implants 100, 800 are that implant 800 does not include a bend or dog leg shape along each leg 830, axes 835 are oriented perpendicular to axis 805 in the un-flexed position, and opposing legs 830 of implant 800 mounted to different distal regions 816 are coaxially aligned in the un-flexed position. In addition, in this embodiment, each axis 835 and central axis 805 are disposed in a common plane in the un-flexed position.

Although bridge 810 is shown in FIG. 16 as only a partial circular or semi-circular shape, in other embodiments, the bridge (e.g., bridge 810) may be a closed loop such as a complete circular or semi-circular shape similar to bridge 110 of implant 10. For example, an embodiment of an implant 900 shown in FIG. 17 is similar to implant 800 except that implant 900 comprises a body 902 that defines a completely circular, closed loop resilient bridge 910 and a plurality of resilient legs 930 extending inwardly from bridge 910. Implant 900 has a central or longitudinal axis 905 passing through a geometrical center of bridge 910 and centered between the pairs of opposed legs 930 in top view. Bridge 910 has a first axial end 910a and a second axial end 910b opposite end 910a. In addition, bridge 910 includes a pair of arcuate shaped first regions 912 that span across central axis 905, a plurality of resilient torsion region 914 from which legs 930 extend, a pair of second regions 916 extending between torsion regions 914 on opposite sides of axis 905. Thus, each first region 912 extends circumferentially between two torsional regions 914 on opposite sides of axis 905, and each second region 916 extends between two torsional regions 914 on the same side of axis 905. Each leg 930 has a central axis 935, a first or fixed end 930a fixably attached to a corresponding torsional region 914, and a second or free end 930a distal bridge 910. In this embodiment, axes 935 are parallel to and laterally spaced apart from axis 905 and opposed legs 930 on the same side of axis 905 are coaxially aligned with implant 900 in the un-flexed position. In addition, in this embodiment, axes 935 and central axis 905 are disposed in a common reference plane in the un-flexed position.

The rounded, closed loop bridges 110, 910 described herein are generally circular or oval. However, in other embodiments, the closed loop bridge may have a different geometry and/or include regions having different radii of curvature. For example, FIG. 18 illustrates an embodiment of an implant 1000 comprising a body 1002 that defines a closed loop, resilient bridge 1010, and a plurality of resilient legs 1030 extending inwardly from bridge 1010. Implant 1000 has a central or longitudinal axis 1005 passing through a geometrical center of bridge 1010 and centered between the pairs of opposed legs 1030 in top view. Bridge 1010 has a first axial end 1010a and a second axial end 1010b opposite end 1010a. In addition, bridge 1010 includes a pair of arcuate shaped first regions 1012 that span across central axis 1005, a plurality of resilient torsion region 1014 from which legs 1030 extend, a pair of second regions 1016 extending between torsion regions 1014 on opposite sides of axis 1005. Thus, each first region 1012 extends circumferentially between two torsional regions 1014 on opposite sides of axis 1005, and each second region 1016 extends between two torsional regions 1014 on the same side of axis 1005. Each leg 1030 has a central axis 1035, a first or fixed end 1030a fixably attached to a corresponding torsional region 1014, and a second or free end 1030a distal bridge 1010. In this embodiment, axes 1035 are parallel to and laterally spaced apart from axis 1005 and opposed legs 1030 on the same side of axis 1005 are coaxially aligned with implant 1000 in the un-flexed position. In addition, in this embodiment, axes 1035 and central axis 1005 are disposed in a common reference plane in the un-flexed position. However, unlike implant 900 in which the outer profile of bridge 910 is generally convex in top view (i.e., regions 912, 914, 916 are bowed outwardly), in this embodiment, the outer profile of bridge 1010 includes convex regions and concave regions in top view. In particular, the outer profile of bridge 1010 in top view is generally convex along regions 1014, 1016, but concave along regions 1012.

In some embodiments, the resilient legs may extend from the bridge different angles and/or have central axes that are not coaxially aligned with each other or the central axis of the implant in the un-flexed position. Such embodiments may be useful when greater than two bone fragments are pulled together as the plurality of leg angles may be configured to impart compressive loads along multiple fractures, osteotomies or arthrodesis sites (e.g., compression 18 across break 12) to enable fusion. For example, FIG. 19 illustrates an embodiment of an implant 1100 that is substantially the same as implant 900 shown in FIG. 17 with the exception that the resilient legs of implant 1100 are oriented differently than legs 930 of implant 900. In particular, implant 1100 comprises a body 1102 that defines a circular, closed loop resilient bridge 1110 and a plurality of resilient legs 1130 extending inwardly from bridge 1110. Implant 1100 has a central or longitudinal axis 1105 passing through a geometrical center of bridge 1110 and centered between two pairs of legs 1130 in top view. Bridge 1110 has a first axial end 1110a and a second axial end 1110b opposite end 1110a. In addition, bridge 1110 includes a pair of arcuate shaped first regions 1112 that span across central axis 1105, a plurality of resilient torsion region 1114 from which legs 1130 extend, and a pair of second regions 1116 extending between torsion regions 1114 on opposite sides of axis 1105. Thus, each first region 1112 extends circumferentially between two torsional regions 1114 on opposite sides of axis 1105, and each second region 1116 extends between two torsional regions 1114 on the same side of axis 1105. Each leg 1130 has a central axis 1135, a first or fixed end 1130a fixably attached to a corresponding torsional region 1114, and a second or free end 1130a distal bridge 1110. However, unlike implant 900, in this embodiment, not all axes 1135 are parallel, no axes 1135 are oriented parallel to central axis 1105, and no pair of legs 1130 are coaxially aligned in the un-flexed position. Rather, in this embodiment, each axis 1135 is offset and non-collinear with respect to the other axes 1135. In the embodiment shown in FIG. 19, axes 1135 and central axis 1105 are disposed in a common reference plane in the un-flexed position.

During use, each leg 1130 may be angularly rotated to change the position of axes 1135 in the manner previously described, thus applying bending and/or torsional stresses to bridge 1110 and/or legs 1130. Due to the rotation angle imparted to each leg 1130, torsional and/or bending stresses arise in regions 1114 on both sides of each leg 1130 and along region 1112, 1116 between legs 1130.

As previously described, one or more of the legs of each implant may each be configured differently. For example, FIG. 20 illustrates an embodiment of an implant 1200 that includes two legs 1230 having a bent or dog leg shape and two legs 1230' that are linear. More specifically, implant 1200 comprises a body 1202 that defines a circular, closed loop resilient bridge 1210 and the plurality of resilient legs 1230, 1230' extending inwardly from bridge 1210. Implant 1200 has a central or longitudinal axis 1205 passing through a geometrical center of bridge 1210 and centered between a first pair of legs 1230, 1230' and a second pair of legs 1230, 1230' in top view. Bridge 1210 has a first axial end 1210a and a second axial end 1210b opposite end 1210a. In addition, bridge 1210 includes a pair of arcuate shaped first regions 1212 that span across central axis 1205, a plurality of resilient torsion region 1214 from which legs 1230, 1230' extend, and a pair of second regions 1216 extending between torsion regions 1214 on opposite sides of axis 1205. Thus, each first region 1212 extends circumferentially between two torsional regions 1214 on opposite sides of axis 1205, and each second region 1216 extends between two torsional regions 1214 on the same side of axis 1205. Each leg 1230' has a central axis 1235', a first or fixed end 1230a' fixably attached to a corresponding torsional region 1214, and a second or free end 1230b' distal bridge 1210. In this embodiment, each axis 1235' is linear between ends 1230a', 1230b'. In contrast, the pair of legs 1230 have dog leg shapes and include a bend. In particular, each leg 1230 has a first or fixed end 1230a fixably attached to a corresponding torsional region 1214 and a second or free end 1230b distal bridge 1210. In addition, each leg 1230 includes a first or upper leg portion 1232 extending from first end 1230a and a second or lower leg portion 1234 extending from upper leg portion 1232 to end 1230b. Upper leg portion 1232 has a central axis 1235 and lower leg portion 1234 has a central axis 1245 oriented at a non-zero leg angle relative to axis 1235. In general, axes 1235, 1245 may be oriented at any suitable leg angle as previously described above for implant 100.

Figure 21:
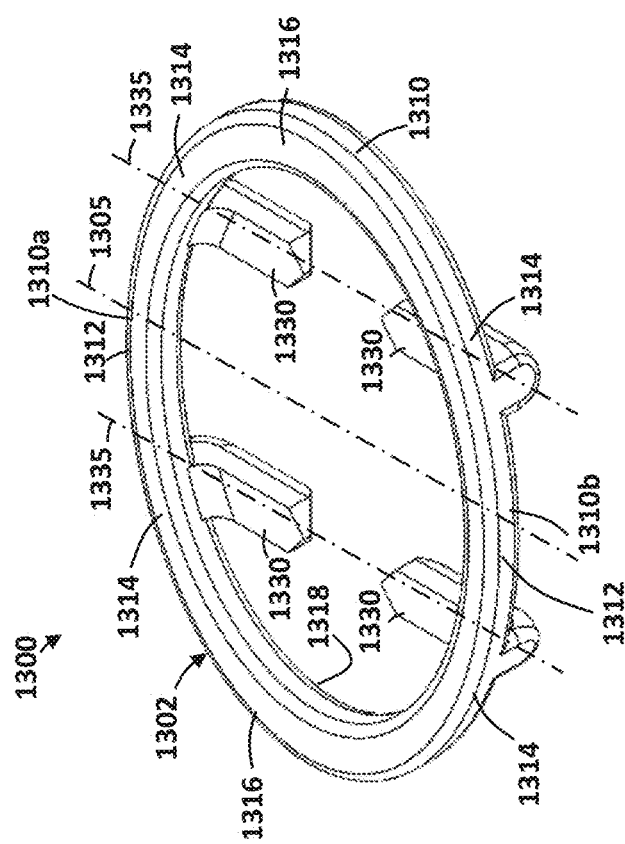

In some embodiments of implants described above (e.g., implants 400, 700, 800, 900, 1000, 1100), the central axis of the implant and the axes of the legs are disposed in a common reference plane in the un-flexed position; whereas in other embodiments of implants described above (e.g., implants 100, 500, 1200), the central axis of the implant and the axes of the legs are not disposed in a common reference plan in the un-flexed position. However, it is also contemplated that some embodiments of implants in accordance with principles described herein may include legs having central axes that are disposed in a common reference plane but the central axis of the implant is not disposed in that common reference plane in the un-flexed position. For example, FIG. 21 illustrates an embodiment of an implant 1300 that includes a plurality of legs 1330 having central axes 1335 that are disposed in a common reference plane that does not also contain the central axis 1305 of implant 1300 in the un-flexed position. More specifically, implant 1300 comprises a body 1302 that defines a circular, closed loop resilient bridge 1310 and the plurality of resilient legs 1330 extending inwardly from bridge 1310. Implant 1300 has a central or longitudinal axis 1305 passing through a geometrical center of bridge 1310 and centered between the two pairs of legs 1330 in top view. Bridge 1310 has a first axial end 1310a and a second axial end 1310b opposite end 1310a. In addition, bridge 1310 includes a pair of arcuate shaped first regions 1312 that span across central axis 1305, a plurality of resilient torsion region 1314 from which legs 1330 extend, and a pair of second regions 1316 extending between torsion regions 1314 on opposite sides of axis 1305. Thus, each first region 1312 extends circumferentially between two torsional regions 1314 on opposite sides of axis 1305, and each second region 1316 extends between two torsional regions 1314 on the same side of axis 1305. Each leg 1330 has a central axis 1335, a first or fixed end 1330a fixably attached to a corresponding torsional region 1314, and a second or free end 1330b distal bridge 1310. In this embodiment, each axis 1335 is linear between ends 1330a, 1330b, and further, axes 1335 are disposed in a common reference plane in the un-flexed position. However, ends 1330a generally extend from the lower surface 1318 of bridge 1310, and thus, the common reference plane containing axes 1335 is parallel to but spaced below central axis 1305. In other words, central axis 1305 is not disposed in the common reference plane within which axes 1335 of legs 1330 are disposed in the un-flexed position. In the manner described, embodiments disclosed herein include staple-style implants that comprise a resilient bridge and a plurality of resilient legs extending from the bridge. The implant is configured to elastically and resiliently transition between an un-flexed position and a flexed position. In general, the bridge and/or legs may elastically and resiliently flex between the un-flexed position and flexed position. The implants store stress(es) (e.g., bending stresses, torsional stresses, or combinations thereof) along one or more portions, which bias implant to the un-flexed position. In addition, some embodiments disclosed may allow surgical applications having holes drilled at a converging angle relative to a reference plane, and thus, may offer enhanced fixation and stability to a fracture, osteotomy, or arthrodesis site to enable fusion. Further, some embodiments may include a bent leg profile or dog leg which provides enhanced fixation for surgical applications which include holes drilled at a converging angle relative to a central axis. Still further, some embodiments having a bent leg profile may be advantageous for implants which are only temporarily implanted in a patient or where revision surgeries are anticipated.

Embodiments of implants disclosed herein (e.g., implants 100, 200, 300, 400, etc.) are generally described as being made of Nitinol. Although Nitinol and its superelastic properties may be particularly preferred, embodiments of implants described herein may alternatively be made of other materials suitable for use as implants and that provide the desired elastic properties. Examples of other materials may include, without limitation, titanium, stainless steel alloys, and PEEK.

While exemplary embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the disclosure. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps.

What is claimed is:

1. A method for installing an orthopedic implant comprising a body and a plurality of legs coupled to the body, the method comprising:
    (a) applying a torsional stress to the body that imparts a first angular displacement between the plurality of legs;
    (b) inserting the plurality of legs into a plurality of holes in a pair of bone segments; and
    (c) releasing the body after (b) such that the torsional stress imparts a second angular displacement between the plurality of legs, wherein the second angular displacement is opposite the first angular displacement.

2. The method of claim 1, comprising compressing the bone segments together as a result of the second angular displacement.

3. The method of claim 1, further comprising:
    (d) applying a bending stress to the body during (b); and
    (e) increasing a distance between the plurality of legs as a result of (d).

4. The method of claim 1, wherein the plurality of holes comprises a first hole in a first of the pair of bone segments and a second hole in a second of the pair of bone segments, wherein the first hole is non-parallel to the second hole.

* * * * *